(12) United States Patent
Abo-Auda et al.

(10) Patent No.: US 12,329,431 B2
(45) Date of Patent: Jun. 17, 2025

(54) DIRECTIONAL KYPHOPLASTY DEVICE AND METHOD OF USING SUCH A DEVICE

(71) Applicant: Cardio Voyage Innovations, LLC, McKinney, TX (US)

(72) Inventors: Wael Abo-Auda, Allen, TX (US); Carlton Craig Cranford, Sherman, TX (US)

(73) Assignee: Cardio Voyage Innovations, LLC, McKinney, TX (US)

( * ) Notice: Subject to any disclaimer, the term of this patent is extended or adjusted under 35 U.S.C. 154(b) by 0 days.

(21) Appl. No.: 18/492,213

(22) Filed: Oct. 23, 2023

(65) Prior Publication Data

US 2024/0216030 A1 Jul. 4, 2024

Related U.S. Application Data

(63) Continuation of application No. 16/957,413, filed as application No. PCT/US2018/067792 on Dec. 28, 2018, now Pat. No. 11,793,560.

(60) Provisional application No. 62/611,134, filed on Dec. 28, 2017.

(51) Int. Cl.
  *A61B 17/88* (2006.01)

(52) U.S. Cl.
  CPC ...... *A61B 17/8855* (2013.01); *A61B 17/8811* (2013.01); *A61B 17/8816* (2013.01); *A61B 17/8819* (2013.01)

(58) Field of Classification Search
  CPC ............ A61B 17/8802; A61B 17/8811; A61B 17/8816; A61B 17/8819; A61B 17/8822; A61B 17/8855; A61B 17/8858
  See application file for complete search history.

(56) References Cited

U.S. PATENT DOCUMENTS

| | | | | |
|---|---|---|---|---|
| 7,666,205 B2* | 2/2010 | Weikel | ............... | A61B 17/7275 606/192 |
| 7,722,620 B2* | 5/2010 | Truckai | ............. | A61B 17/8822 606/93 |
| 8,876,833 B2* | 11/2014 | Donovan | ........... | A61B 17/8827 606/92 |
| 9,554,840 B2* | 1/2017 | Druma | ............... | A61B 17/8822 |
| 2002/0156482 A1* | 10/2002 | Scribner | ............ | A61B 17/8855 606/92 |
| 2009/0299282 A1* | 12/2009 | Lau | ................... | A61M 25/0136 604/99.01 |
| 2013/0218164 A1* | 8/2013 | Mueller | ............. | A61B 17/8858 606/93 |

(Continued)

*Primary Examiner* — Anu Ramana
(74) *Attorney, Agent, or Firm* — The Webb Law Firm

(57) ABSTRACT

A device for correcting a compression-type fracture including a housing at a proximal end of the device, a cannula extending from the housing and through a directional balloon, and a tip at a distal end of the cannula, wherein the cannula has an outer tube for supplying fluid to the balloon and an inner tube positioned within the outer tube for supplying cement through at least one opening in the distal end of the cannula. A method of using the device where the device is inserted into a fracture site, the balloon is inflated to elevate fragments of the fracture, cement is injected into the opening created by elevating the fragments of the fracture and the device is removed from the fracture site. The balloon may be deflated before the injection of the cement or simultaneous with the injection of the cement.

17 Claims, 23 Drawing Sheets

(56) References Cited

U.S. PATENT DOCUMENTS

2015/0342660 A1\* 12/2015 Nash ..................... A61B 18/02
606/21

\* cited by examiner

| CONFIGURATION | THUMB WHEEL | RADIAL PORTS | AXIAL PORTS |
|---|---|---|---|
| CLOSED | 84 (CLOSED) | 44, 96, 16, 18, 100 | 100, 18 |

FIG.11A

| CONFIGURATION | THUMB WHEEL | RADIAL PORTS | AXIAL PORTS |
|---|---|---|---|
| AXIAL INJECTION | 84 (AXIAL) | 44, 96, 16, 18, 100 | 100, 18, 76 |

FIG.11B

| CONFIGURATION | THUMB WHEEL | RADIAL PORTS | AXIAL PORTS |
|---|---|---|---|
| RADIAL INJECTION | 84 (RADIAL) | 44, 96, 16, 18, 100 | 100, 18 |

FIG.11C

DIRECTIONAL KYPHOPLASTY DEVICE AND METHOD OF USING SUCH A DEVICE

CROSS-REFERENCE TO RELATED APPLICATIONS

This application is a continuation of U.S. patent application Ser. No. 16/957,413, now U.S. Pat. No. 11,793,560, filed Dec. 28, 2018, which is the United States national phase of International Application No. PCT/US2018/067792 filed Dec. 28, 2018, and claims priority to U.S. Provisional Patent Application No. 62/611,134, filed Dec. 28, 2017, the disclosures of which are hereby incorporated by reference in their entirety.

BACKGROUND OF THE INVENTION

Field of the Invention

The present invention is directed to a device for correcting compression-type fractures, including intra-articular fractures in which the break crosses into the surface of a joint, especially in the ankle or heel, and a method of using such a device to correct compression-type fractures.

Description of Related Art

Ankle fractures are among the most commonly sustained fractures, with over five million ankle injuries reported annually in the United States. Heel or calcaneal fractures, while less common, are often even more debilitating. These fractures are typically of the intra-articular type, in which the fracture breaches into the surface across a joint, and thus requires especially careful management. Although intra-articular fractures do not appear much different than those that occur outside of a joint space, they are associated with long-term complications that are difficult to assuage. Treating these fractures necessitates comprehensive consideration and maintenance of bone fragment positions and related ligament attachments, limiting options for intervention. Without treatment, however, intra-articular injuries may lead to stiffness, deformity, pain, and posttraumatic arthritis.

The calcaneus is the most frequently injured tarsal bone, accounting for 60% of tarsal fractures occurring in adults. Intra-articular fractures are the more prevalent category of calcaneus fractures following a traumatic injury, making up 60-75% of all calcaneal fractures. 72% of these fractures were a result of a fall from a height, an injury which can be difficult to recover from and often results in a lifelong disability. This is further damaging to a patient's economic welfare, as symptoms may affect the ability to perform manual labor. These fractures have an annual incidence rate of approximately 11.5 per 100,000 people, with male patients representing the majority.

The surgical treatment path for intra-articular fractures of the ankle has become the preferred approach in the past two decades due to advanced surgical instrumentation and enhanced technique. Developments in minimally invasive procedures have resulted in improved recovery times as well as long-term symptom reduction. Operations a patient undergoes for these fractures are primarily focused on avoiding deformity and stiffness. For these purposes, it is necessary to secure an anatomical reduction of the articular surface and to restore joint stability and normal axial alignment. Achieving this with depressed articular fragments requires maintaining the corrective elevation throughout the healing process. Currently, the most common method of support is filling the subchondral void with an autologous or allogeneic bone transplant; this method often provides insufficient support for weight and prevents patients from accepting weight on the injured site for 6-12 weeks post-operation. Donor-site morbidity is another potential problem with bone grafting surgeries that can result in severe complications as well as longer recovery times.

Balloon kyphoplasty is a minimally invasive method of surgery typically performed in place of percutaneous vertebroplasty for the treatment of spinal compression fractures. This procedure makes use of a small, reinforced balloon that is guided into the vertebrae using fluoroscopy then inflated in order to lift bone fragments into their correct position. The balloon is subsequently deflated and retracted, and the void left behind by the balloon is filled with a cement to keep the fragments in place and stabilize the bone. This allows for greater control in the correction and removes the need for grafts, reducing the likelihood of procedure failure. In applying the principles of this procedure to fracture corrections, it should be noted that a balloon and device design emphasizing the physical direction of the correction significantly enhances the level of control the operator has in the elevation of the depressed articular fragment. Current kyphoplasty methods and devices offer poor directional reduction control. In addition, while performing kyphoplasty, the operator must exchange the instrument in use relatively frequently for the various steps of the procedure; this extends the time of operation and introduces room for surgical error.

Such kyphoplasty has several drawbacks. First, the balloon used to elevate the bone fragments is non-directional (spherical). Second, more than one device is used during the procedure necessitating in multiple exchanges of the devices during the procedure. Third, the elevation of the fracture and the introduction of the cement cannot be controlled simultaneously.

Therefore, there is a need for new methods of safe, effective, and precise correction of intra-articular fractures of the ankle that corrects for these drawbacks.

SUMMARY OF THE INVENTION

The present invention is directed to a device for and method of correcting compression-type fractures, including intra-articular compression-type ankle or heel fractures, using adjustable and/or controllable directional balloon kyphoplasty. The device allows for elevation of the fragments and injection of bone cement into the fracture to be accomplished using a single device thereby reducing the number of device exchanges required to complete the procedure. Directionality of the elevation of the fragments may be obtained using a balloon, such as, but not limited to an oblong balloon. When this balloon is inflated, it provides structural volume within the fracture into which specialized bone cement may be injected to optimally support the elevated bone fragments. Balloon inflation and cement injection are done via a cannula preloaded with the balloon, with a single mechanism facilitating both. The device makes use of an ergonomic hand grip used for all steps of the procedure, allowing for single-handed device operation.

In accordance with an embodiment of the present invention, a device for correcting an intra-articular compression fracture includes a housing including a fluid portion containing a fluid and a cement portion containing a cement; a cannula extending from the housing and including a first passageway and a second passageway; and a balloon engaged with a portion of the cannula, wherein with the device in a first position, the first passageway is in communication with the fluid portion so that the fluid is flowable to the balloon, and wherein with the device in a second position, the second passageway is in communication with the cement portion so that the cement is flowable out of a portion of the cannula.

In one configuration, with the device in a third position, the first passageway is not in communication with the fluid portion and the second passageway is not in communication with the cement portion. In another configuration, with the device in the first position, the second passageway is not in communication with the cement portion. In yet another configuration, with the device in the second position, the first passageway is not in communication with the fluid portion. In one configuration, the balloon is transitionable between an inflated state and a deflated state. In another configuration, the balloon is elongated such that a length of the balloon in a direction parallel to a longitudinal axis of the cannula is longer than a width of the balloon in a direction transverse to the longitudinal axis of the cannula. In yet another configuration, the second passageway includes a cap at a distal end thereof and the cap has an axial opening and a radial opening. In one configuration, with the device in the second position, the second passageway is in communication with the cement portion so that the cement is flowable out of at least one of the radial opening and the axial opening. In another configuration, the radial opening and the axial opening are located between the balloon and a distal end of the cannula. In yet another configuration, the device includes a tip at a distal end of the cannula.

In accordance with another embodiment of the present invention, a device for correcting an intra-articular compression fracture includes a housing at a proximal end of the device; a cannula extending from the housing and through a directional balloon; and a tip at a distal end of the cannula, wherein the cannula comprises an outer tube for supplying fluid to the balloon and an inner tube positioned within the outer tube for supplying cement through at least one of an axial opening and a radial opening in the distal end of the cannula.

In one configuration, the inner tube is coaxial with the outer tube and a first passageway is defined through the inner tube and a second passageway is defined between the inner tube and the outer tube. In another configuration, the inner tube is rotatable with respect to the outer tube and the tip. In yet another configuration, the inner tube includes a cap at a distal end thereof and the cap has an axial opening and a radial opening. In one configuration, the tip includes an axial opening and the outer tube of the cannula includes a radial opening. In another configuration, depending on the position of the inner tube with respect to the outer tube and the tip, at least one of the radial opening and the axial opening is blocked by the outer tube or the tip. In yet another configuration, the device further comprises a thumb wheel connected to the inner tube and used to rotate the inner tube. In one configuration, the thumb wheel can rotate the inner tube into one of three positions: a first position where the radial opening of the cap is not aligned with the radial opening of the outer tube and the axial opening of the cap is not aligned with the axial opening of the tip; a second position where the radial opening of the cap is aligned with the radial opening of the outer tube and the axial opening of the cap is not aligned with the axial opening of the tip; and a third position where the radial opening of the cap is not aligned with the radial opening of the outer tube and the axial opening of the cap is aligned with the axial opening of the tip. In another configuration, the balloon is elongated such that a length of the balloon in a direction parallel to a longitudinal axis of the cannula is longer than a width of the balloon in a direction transverse to the longitudinal axis of the cannula. In yet another configuration, the outer tube has a hole through which a fluid passes from the second passageway into the balloon. In one configuration, the device includes a retractable shield that is coaxial with the cannula and covers the cannula and the balloon. In another configuration, the device includes a handle associated with the housing and connected to a proximal end of the shield, wherein movement of the handle in a proximal direction moves the shield exposing the balloon and a distal portion of the cannula. In yet another configuration, the device includes a regulator for controlling the flow of fluid and/or cement into the cannula.

In accordance with another embodiment of the present invention, a method of correcting a compression-type fracture, such as an intra-articular compression fracture, includes inserting the device into a fracture site; inflating the directional balloon with a fluid supplied through the second passageway to elevate fragments of the fracture; injecting cement from the first passageway into the opening created by elevating the fragments of the fracture; and removing the device from the fracture site, wherein the balloon is deflated before the injection of the cement or simultaneous with the injection of the cement.

In one configuration, the cement is injected in at least one of an axial direction and a radial direction. In another configuration, the balloon is elongated such that a length of the balloon in a direction parallel to a longitudinal axis of the cannula is longer than a width of the balloon in a direction transverse to the longitudinal axis of the cannula. In yet another configuration, the device includes a retractable shield that is coaxial with the cannula and covers the cannula and the balloon, and the shield is retracted to expose the balloon and a distal portion of the cannula prior to inflating the balloon.

In accordance with another embodiment of the present invention, a method of correcting a compression-type fracture, such as an intra-articular compression fracture, includes elevating bone fragments of the fracture to create a space; and filling the space with bone cement, wherein the space created by the elevation of the bone fragments has directionality.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 11A is a view of a first position for a thumb wheel of a device in accordance with an embodiment of the present invention.

FIG. 11B is a view of a second position for a thumb wheel of a device in accordance with an embodiment of the present invention.

FIG. 11C is a view of a third position for a thumb wheel of a device in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DESCRIPTION OF THE INVENTION

Figure 1:
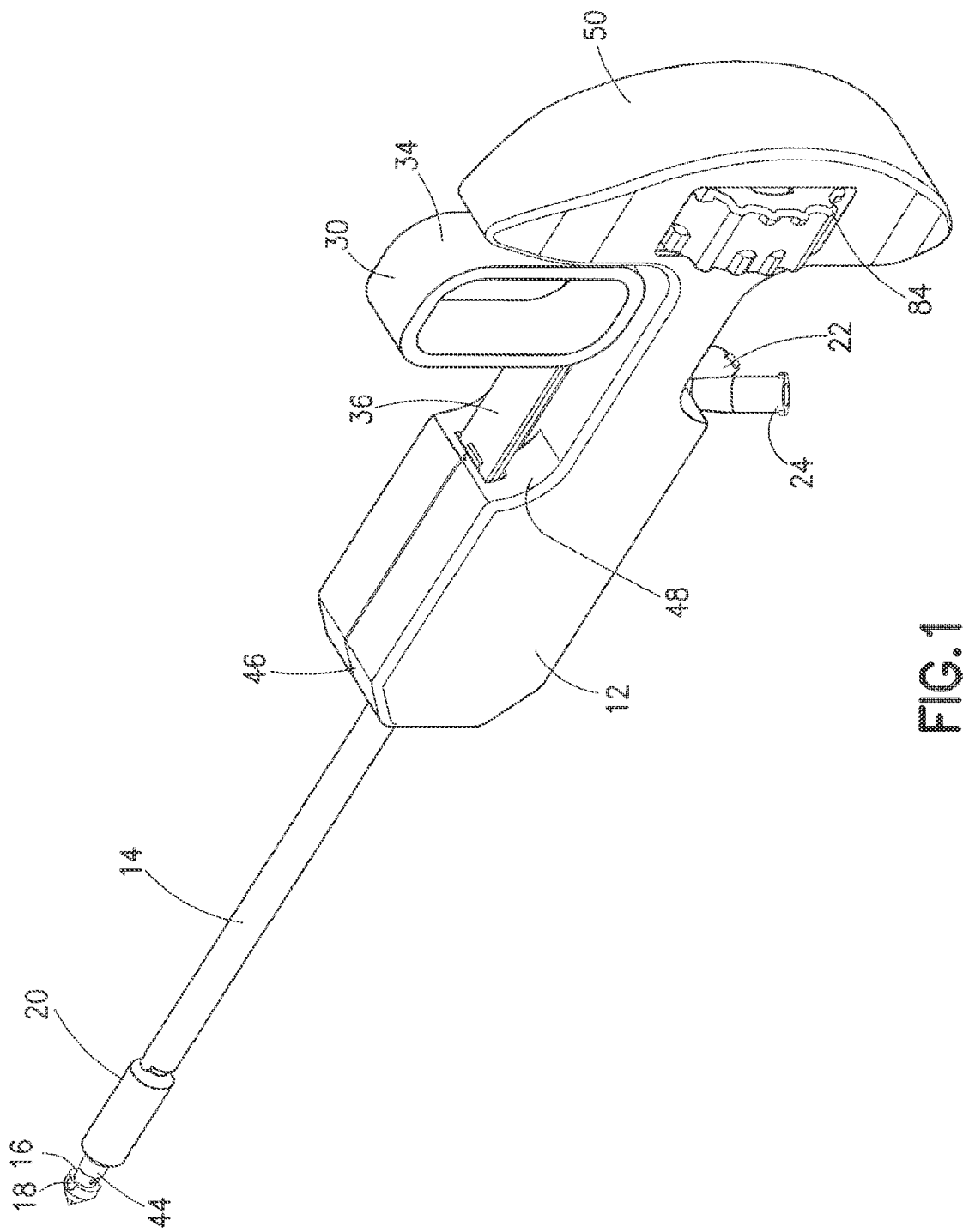
FIG. 1 is a perspective view of a device in accordance with an embodiment of the present invention.
Figure 2:
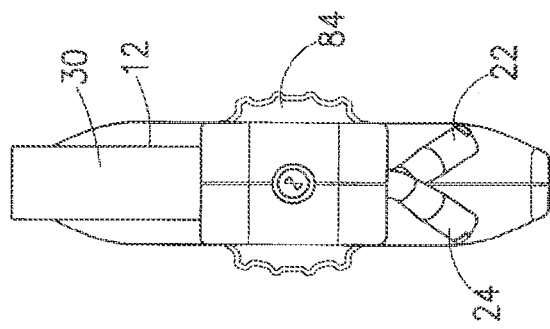
FIG. 2 is a rear elevation view of a device in accordance with an embodiment of the present invention.
Figure 3:
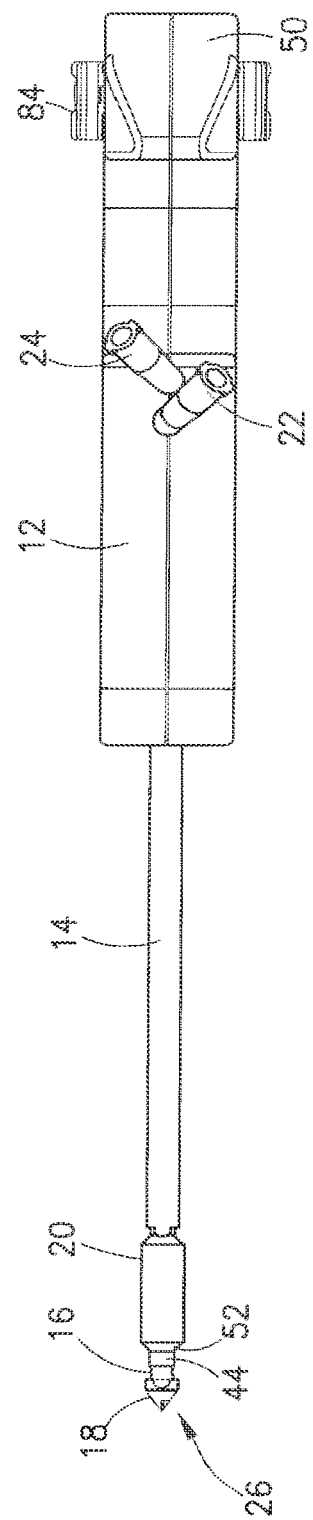
FIG. 3 is a bottom elevation view of a device in accordance with an embodiment of the present invention.
Figure 4:
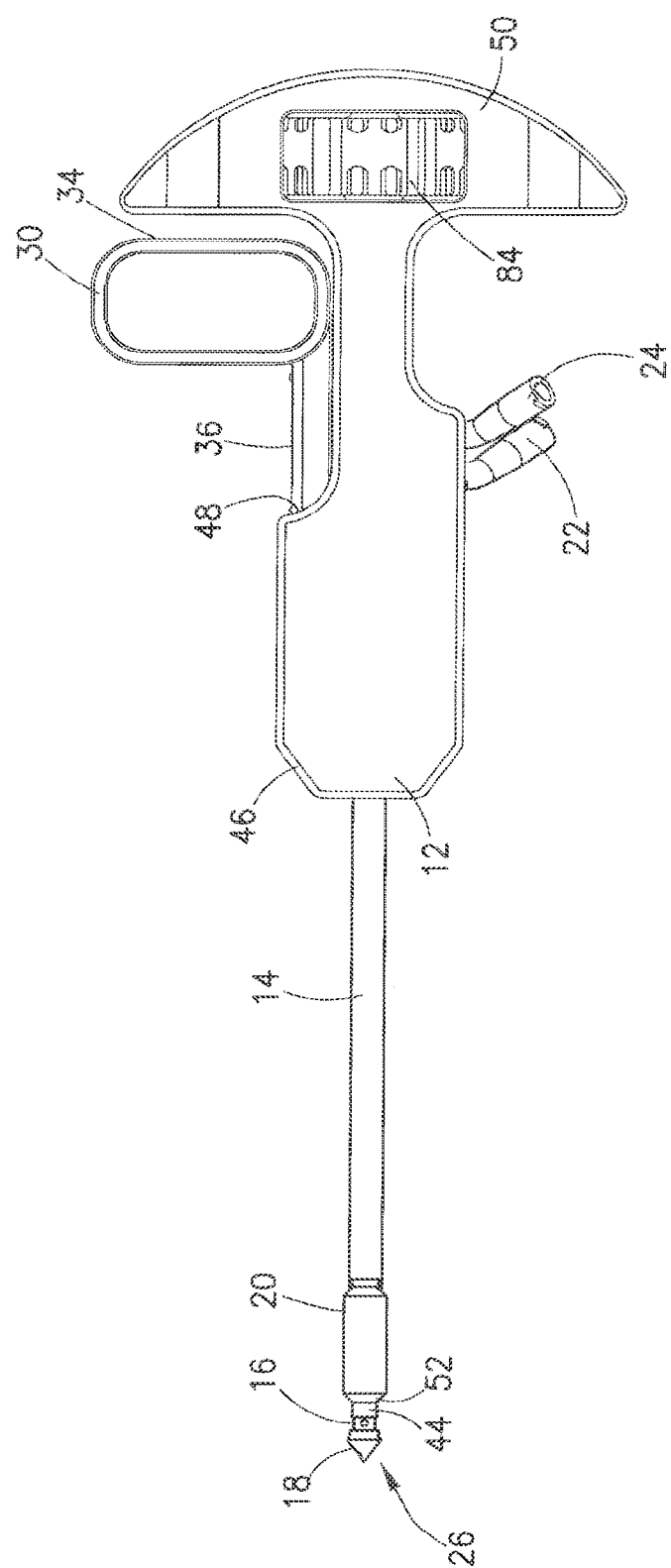
FIG. 4 is a side elevation view of a device in accordance with an embodiment of the present invention.
Figure 5:
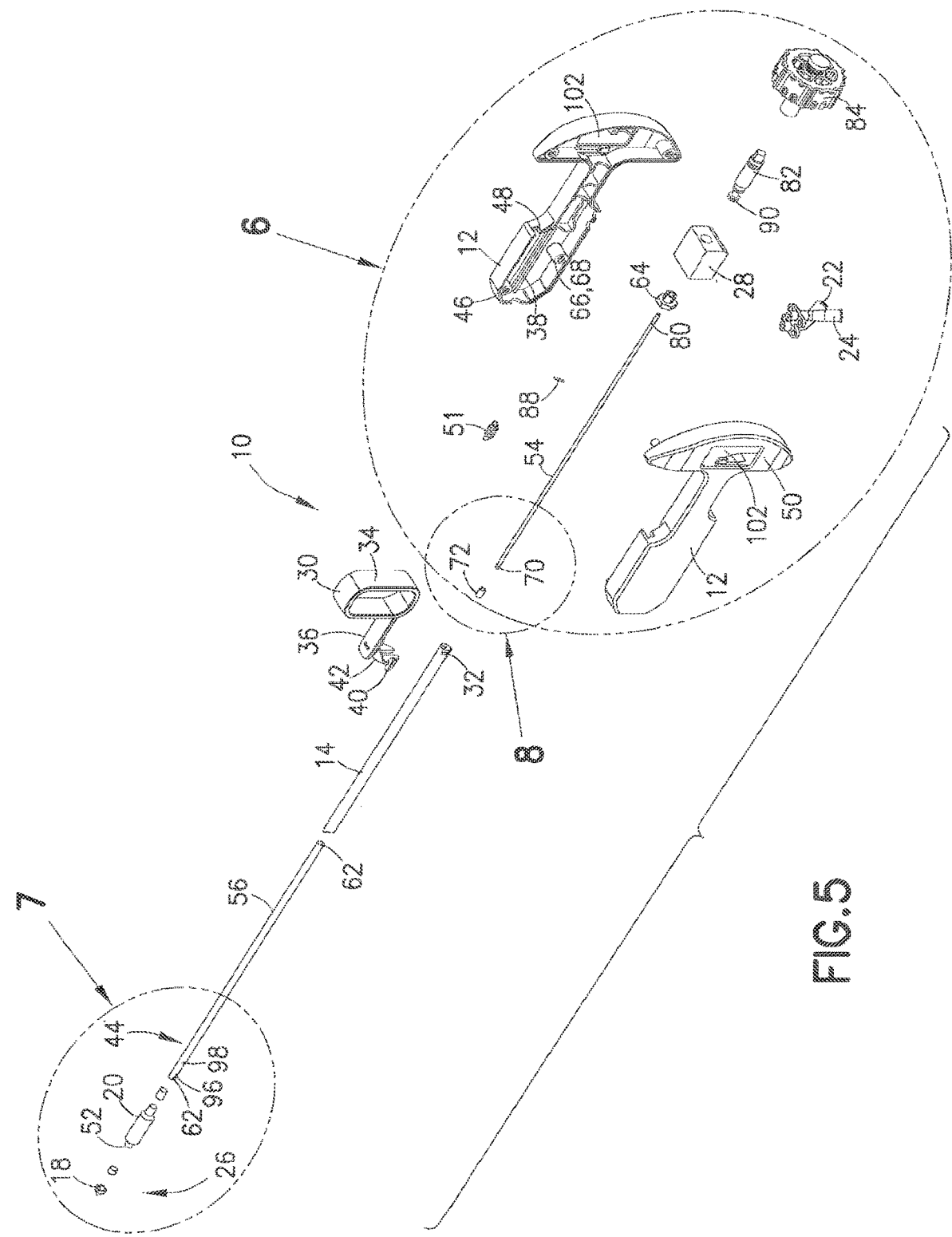
FIG. 5 is an exploded perspective view of a device in accordance with an embodiment of the present invention.
Figure 6:
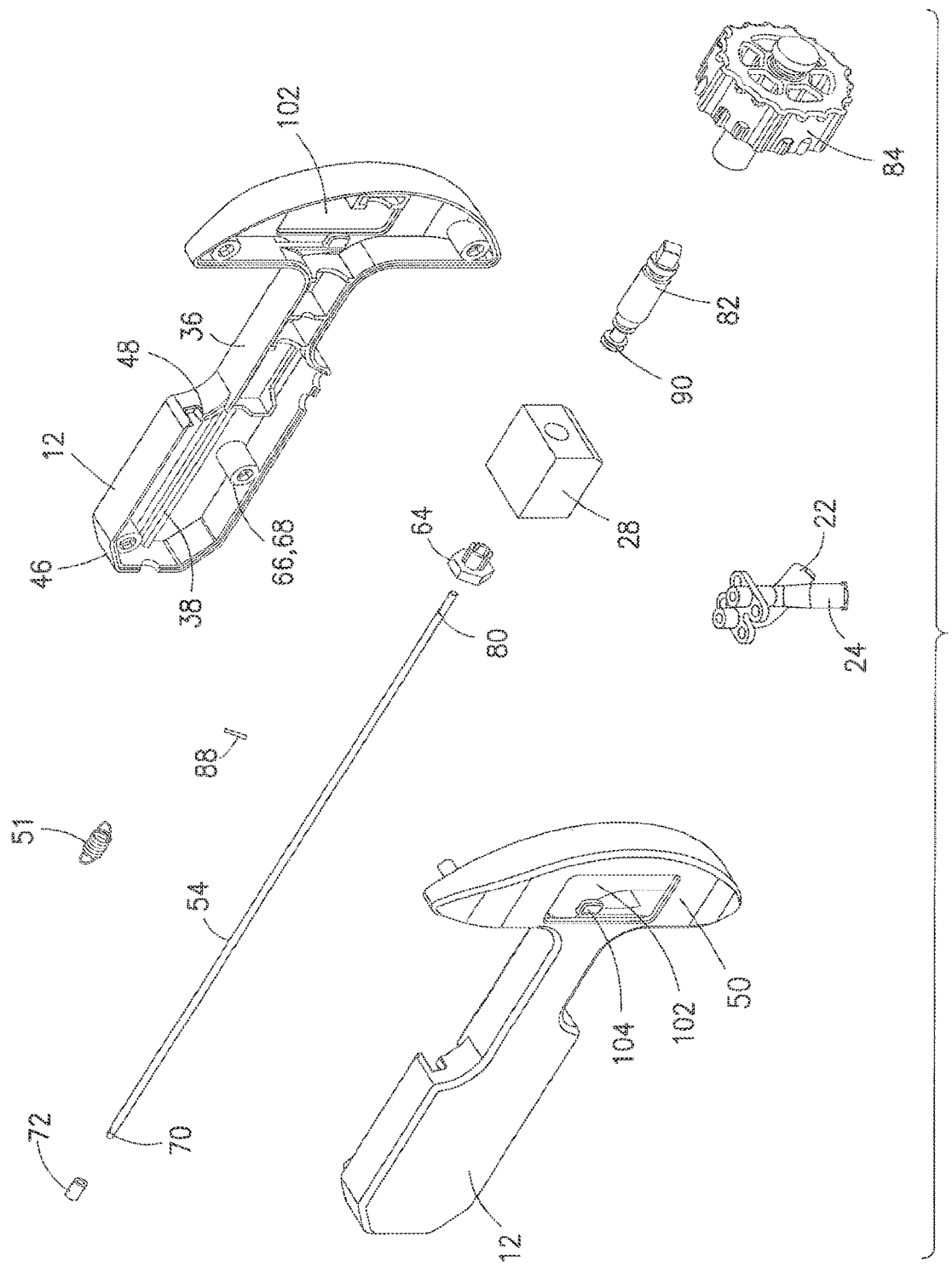
FIG. 6 is an enlarged exploded perspective view of the device shown in circle 6 in FIG. 5 in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The present invention relates to a device for and a method of compression-type fracture correction, including but not limited to intra-articular compression-type fracture correction, that utilizes an expander adapted for directional reduction. The present invention provides for elevating the fracture in one direction, by use of an inflatable balloon, as will be described herein, to avoid expanding the fracture fragments in non-desired directions within the fracture. The inventive device may provide an all-in-one housing for balloon deployment and cement delivery, as will be described herein, which may allow for one-hand control of the operation, which maximizes operation success and reduces procedure time and the need for multiple device exchanges. In certain embodiments, as will be described herein, maintenance of fracture reduction by elevation during cement delivery to the site can be achieved. As will be discussed herein, simultaneous control of the balloon between the inflated and deflated states, is coupled with cement flow to the site which is guided by fracture reduction pressure.

In the inventive method, the reduction of the fracture is directional, i.e., a non-spherical space is created in the fracture. The space, created by a directional expander, may have a dimension in one direction that is a different size from its dimension in another direction or may include an area having a shape and/or size that is different from the shape and/or size of another area.

The inventive device allows the directional expander to be placed in a fracture where it elevates the fragments of the fracture creating a space into which bone cement is injected to stabilize the fracture, which is all done using a single device, thereby reducing the number of separate instruments required for intra-articular compression fracture correction using prior art kyphoplasty methods. The inventive device and method may be used for correcting fractures in the heel and ankle, especially calcaneal, tibial, talus, ankle, and Pilon or Plafond type fractures.

Further, the fracture reduction and the cement delivery may by simultaneously controlled.

These and other features will become readily apparent from the following detailed description wherein embodiments of the invention are shown and described by way of illustration. As will be realized, the invention is capable of other and different embodiments and its several details may be capable of modifications in various respects, all without departing from the invention. Accordingly, the drawings and description are to be regarded as illustrative in nature and not in a restrictive or limiting sense.

The device 10, shown in FIGS. 1-10, comprises a housing 12, a shield 14, a cannula 16, a tip 18, and a balloon 20. The housing 12 includes a first fluid inlet 22 for providing a fluid, such as saline S, that is used to expand the balloon 20 and a second cement inlet 24 for providing bone cement C that will be expelled from the distal end 26 of the device 10. A connection box 28 is provided through which fluid pathways from the fluid inlet 22 and the cement inlet 24 to the cannula 16 are established.

The cannula 16 extends from the housing 12 to the tip 18 located at the distal end 26 of the device 10. The balloon 20 is provided near the distal end 26 of the device 10 proximal to the tip 18 and spaced from the tip 18. The cylindrical shield 14 surrounds and covers the cannula 16 and the balloon 20. When the shield 14 is retracted, the balloon 20 and a distal portion 44 of the cannula 16 extend from a distal end 52 of the balloon 20 so the tip 18 is exposed.

The housing 12 also has a slide action handle 30 that is attached to a proximal end 32 of the shield 14. The handle 30 has a gripping portion 34 adapted to be engaged by the user to pull the handle 30 in the proximal direction indicated by the arrow. The gripping portion 34 may have any suitable shape that will allow the handle 30 to be easily retracted by the fingers of the user during single handed operation of the device 10, for example, oval or square. A longitudinal bar 36 extends from the gripping portion 34 of the handle 30. The bar 36 rides along a track 38 in the housing 12 when the handle 30 is retracted. The bar 36 includes stoppers 40. Arms 42 extending perpendicularly from the bar 36 are connected to the proximal end 32 of the shield 14. Retraction of the handle 30 in the proximal direction pulls the shield 14 in the proximal direction exposing the distal portion 44 of the cannula 16 and the balloon 20. The length of the bar 36 and the position of the stoppers 40 are set such that the stoppers 40 contact a distal portion 46 of the housing 12 when the shield 14 is in a closed distal position where it covers the balloon 20 and the distal portion 44 of the cannula 16 and contact a proximal portion 48 of the housing 12 to stop proximal movement of the handle 30 when the balloon 20 and the distal portion 44 of the cannula 16 have been exposed. The bar 36 may be connected to a biasing member 51, such as a spring, that is also connected to the housing 12. The biasing member 51 urges the handle 30 and, therefore, the shield 14 towards the closed position and increases the level of control the user has over the retraction of the shield 14.

The housing 12 may be generally T-shaped with a grip 50 extending perpendicular to the longitudinal axis of the device 10 so that the user need only use one hand to operate the device 10. The grip 50 may include an arced outer surface to provide a comfortable fit within the palm of the user's hand. In operation, the user holds the device 10 using the grip 50 with one or more fingers stabilizing the device 10 from the bottom. One or more of the user's fingers near the top of the device 10 are used to retract the handle 30 to expose the balloon 20 and the distal portion 44 of the cannula 16.

Figure 10:
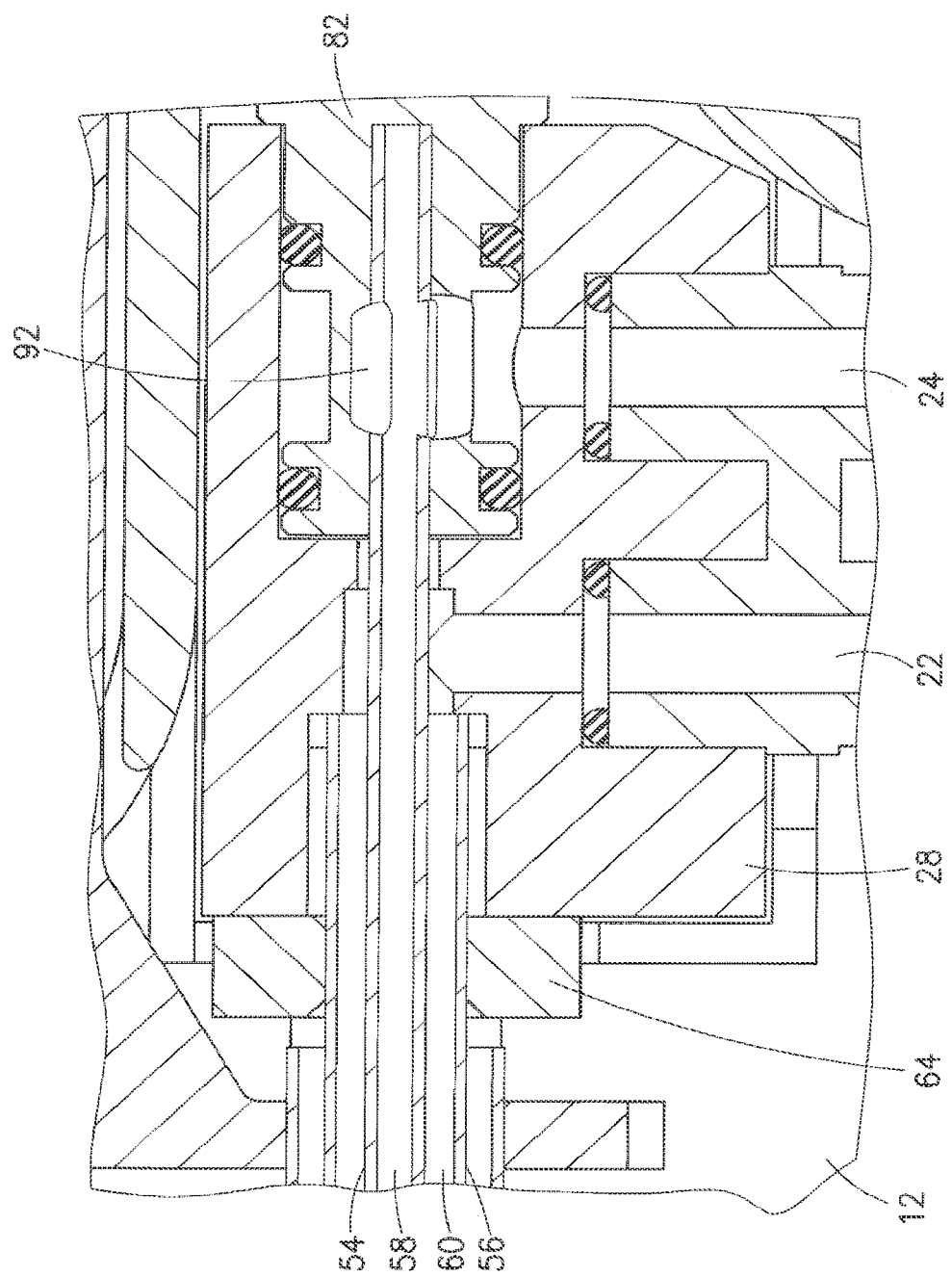
FIG. 10 is an enlarged exploded perspective view of the device shown in circle 10 in FIG. 9 in accordance with an embodiment of the present invention.

The cannula 16 comprises an inner cement tube 54 and an outer fluid tube 56 that surrounds the inner cement tube 54 (see FIG. 10). The inner cement tube 54 and the outer fluid tube 56 are coaxial. The inner cement tube 54 provides a passageway 58 through the cannula 16 for the flow of cement C from the housing 12 to the tip 18. A second passageway 60 for the flow of fluid to the balloon 20 is provided between the outer surface of the inner cement tube 54 and the inner surface of the outer fluid tube 56. The cannula 16 extends through the balloon 20. A distal end 62 of the outer fluid tube 56 is attached to tip 18, and the inner cement tube 54 is configured to rotate within the outer fluid tube 56.

Structural supports 64 are provided in the housing 12 to keep the cannula 16 stable and maintain the relative position of outer fluid tube 56 and the inner cement tube 54. The housing 12 is kept solidly together using cylinder pegs 66 and holes 68 that engage one another.

Figure 8:
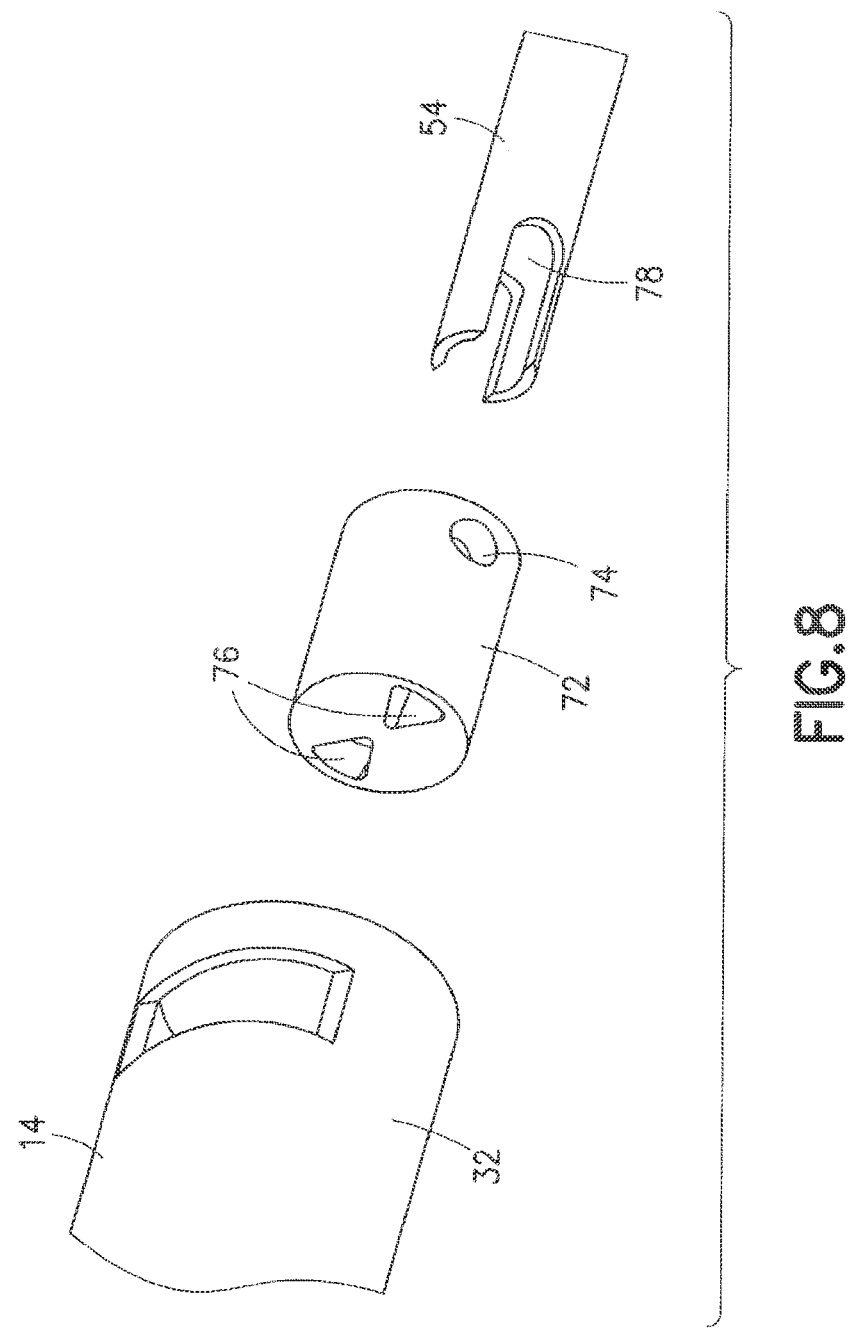
FIG. 8 is an enlarged exploded perspective view of the device shown in circle 8 in FIG. 5 in accordance with an embodiment of the present invention.
Figure 9:
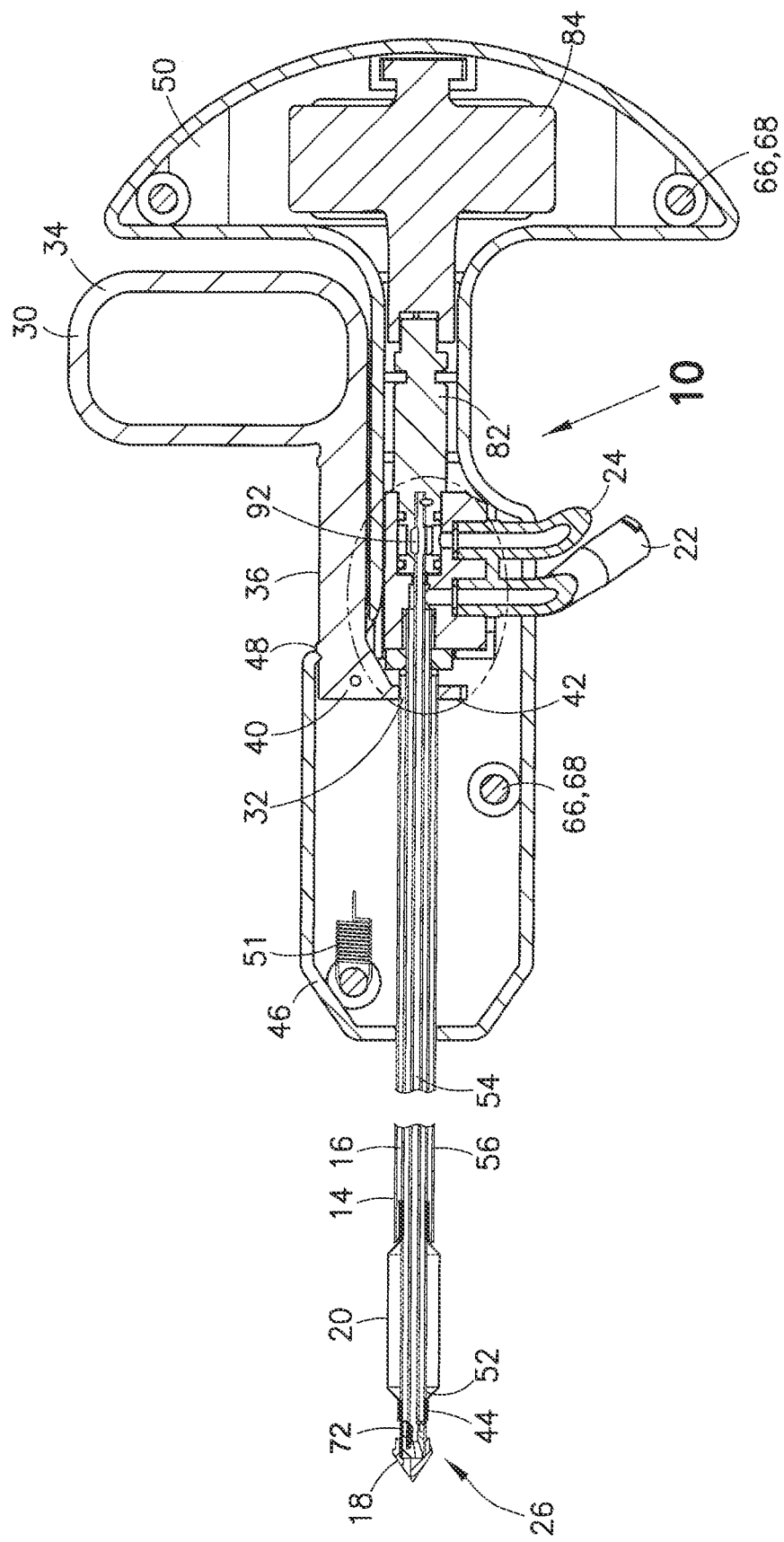
FIG. 9 is a cross-sectional view of the device shown in FIG. 4 in accordance with an embodiment of the present invention.

A distal end 70 of the inner cement tube 54 is covered by a generally cylindrical cap 72 having at least one radial opening 74 extending radially through the outer sidewall and a least one axial opening 76 extending longitudinally through the end of the cap 72 (see FIG. 8). Corresponding openings 78 are provided in the distal end 70 of the inner cement tube 54 to allow cement C to flow from the inner cement tube 54 through the radial openings 74 in the cap 72. The radial openings 74 may take any suitable shape, for example circular, oval, or other shapes, and the axial openings 76 may all take any suitable shape, for example, triangular, oval, or other shapes.

A proximal end 80 of the inner cement tube 54 is connected to a valve member 82 that is in turn attached to a thumb wheel 84 that is used to rotate the inner cement tube 54 relative to the outer fluid tube 56 and the tip 18. The inner cement tube 54 and the valve member 82 each may be provided with a transverse hole through which a pin 88 may be placed to connect the inner cement tube 54 to the valve member 82. A distal end 90 of the valve member 82 extends into the connection box 28. The proximal end 80 of the inner cement tube 54 includes at least one opening 92 that is adapted to connect the cement inlet 24 to the inner cement tube 54 via the valve member 82.

Figure 7:
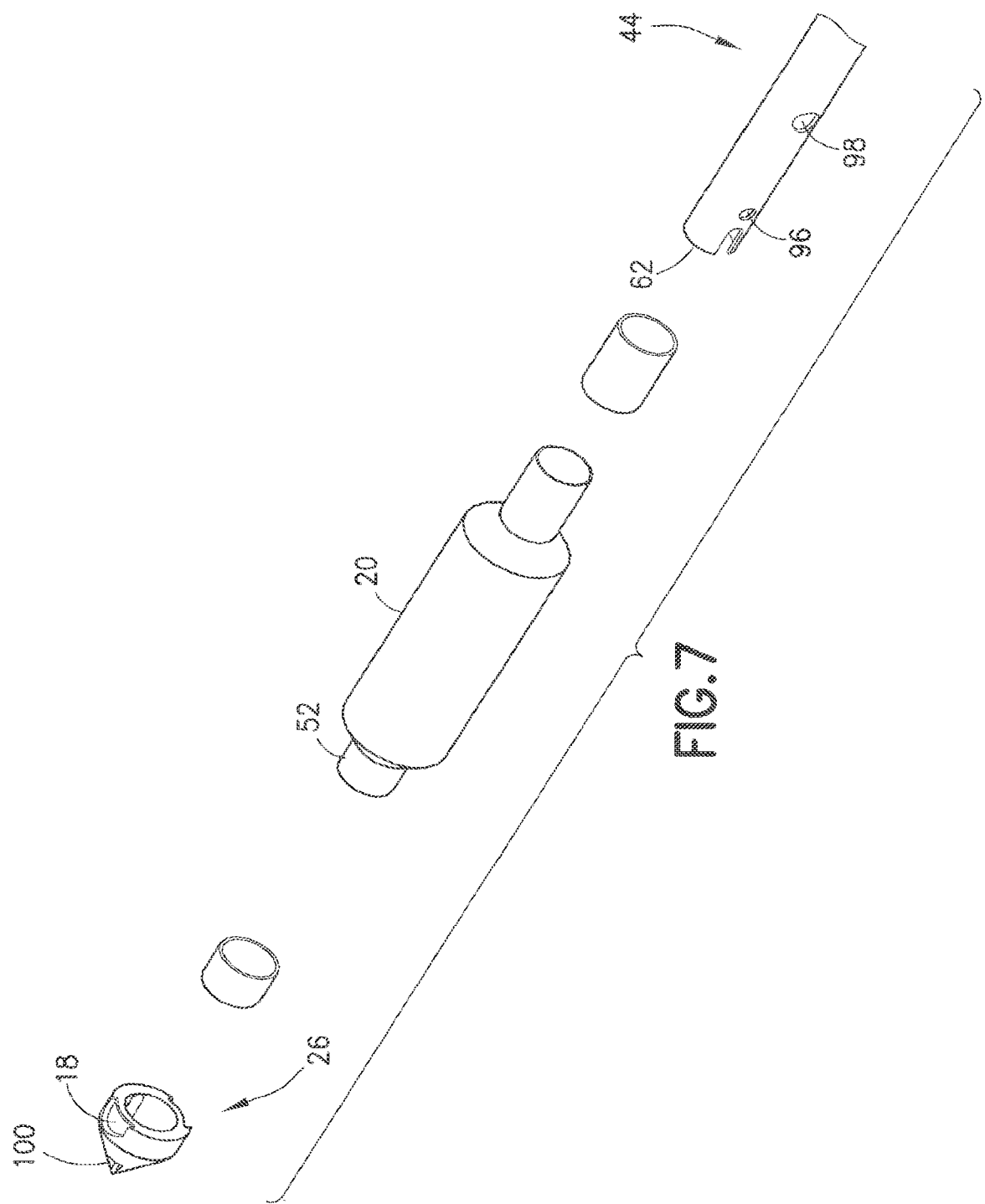
FIG. 7 is an enlarged exploded perspective view of the device shown in circle 7 in FIG. 5 in accordance with an embodiment of the present invention.

The distal end 62 of the outer fluid tube 56 has at least one opening 96 that is adapted to align with the radial openings 74 in the cap 72 of inner cement tube 54 such that alignment of the openings 74 in the outer fluid tube 56 with the radial openings 74 in the cap 72 of the inner cement tube 54 allows cement C to be ejected from the distal portion 44 of the cannula 16 in a radial direction (see FIG. 7). The outer fluid tube 56 also includes at least one opening 98 positioned within the balloon 20 to allow fluid to flow from the outer fluid tube 56 into the balloon 20 (sec FIG. 7).

The tip 18 has at least one opening 100 that is adapted to align with the axial opening 76 in the inner cement tube 54 such that alignment of the opening 100 in the tip 18 allows the cement C to be ejected from tip 18 in an axial direction (see FIG. 7). The openings 100 in the tip and the axial openings 76 in the cap 72 are located off center from the longitudinal axis of the cannula 16 such that alignment of the openings 100 in the tip 18 and the axial openings 76 in the cap 72 is achieved by rotating the inner cement tube 54 relative to the tip 18.

All of the openings for cement injection 74, 76, 78, 96, 100 are provided in the portion of device 10 that is located between the balloon 20 and the distal end 26 of the device 10. In this manner, cement C may be injected into the opening in the fracture created by the balloon 20 while the balloon 20 is still at least partially inflated. This allows the elevation of the fragments within the fracture to be maintained more precisely as the cement C is injected and the device 10 is advanced out of the fracture, thereby decreasing the likelihood of procedure failure and reducing procedure time.

The thumb wheel 84 is substantially hexagonal such that two opposing sides of the thumb wheel 84 extend from openings 102 in opposing sides of the housing 12. The thumb wheel 84 is rotated to place the inner cement tube in one of three positions—closed, axial, and radial. The thumb wheel 84 is locked into each position by the engagement of tabs 104 provided in the openings 102 that interact with recesses in the distal surface of the thumb wheel 84. Ramped surfaces are provided between the recesses such that increased force is required to overcome the ramped portions. However, once sufficient force is provided, the tabs 104 overcome the ramped portions and engage the recessed areas provided between the ramped portions.

As shown in FIG. 11A, in the closed position, the axial openings 76 in the cap 72 of the inner cement tube 54 are not aligned with the openings 100 in the tip 18, and the openings 96 at the distal end 62 of the outer fluid tube 56 are not aligned with the radial openings 74 in the inner cement tube 54. In this position, no cement C may be ejected from the distal end 26 of the device 10.

As shown in FIG. 11B, in the axial position, the axial openings 76 in the cap 72 of the inner cement tube 54 are aligned with the openings 100 in the tip 18, but the openings 96 at the distal end 62 of the outer fluid tube 56 are not aligned with the radial openings 74 in the inner cement tube 54. In this position, cement C may be axially ejected from the distal end 26 of the device 10.

As shown in FIG. 11C, in the radial position, the axial openings 76 in the cap 72 of the inner cement tube 54 are not aligned with the openings 100 in the tip 18, but the openings 96 at the distal end of the outer fluid tube 56 are aligned with the radial openings 74 in the inner cement tube 54. In this position, cement C may be radially ejected from the distal end 26 of the device 10.

Also, in at least the axial and the radial positions, the opening 92 in the valve member 82 is aligned with the cement inlet 24 to provide the cement C that is ejected from the distal end 26 of the device 10.

Figure 15:
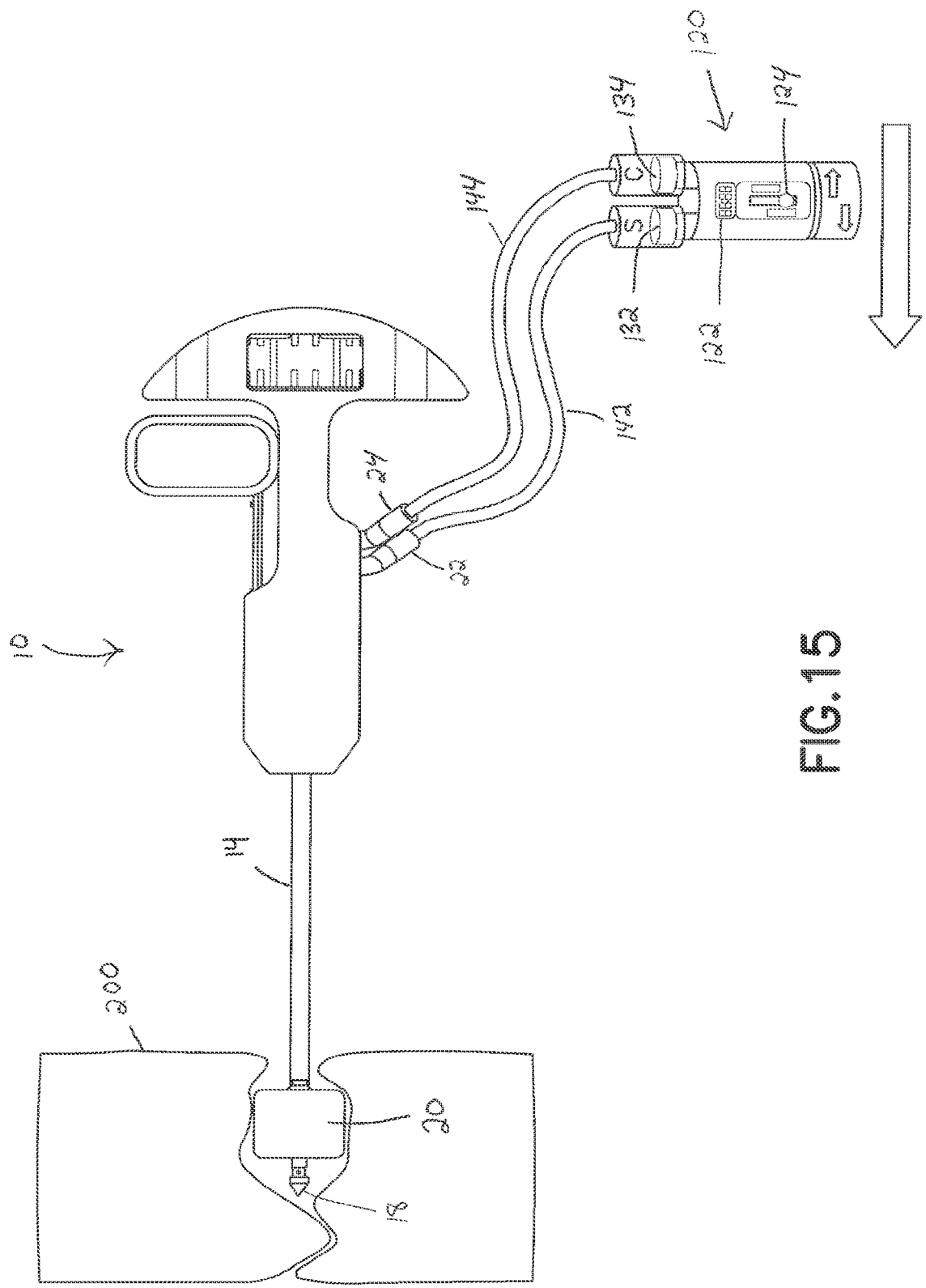
FIG. 15 is a perspective view of a third step of using a device of the present disclosure in accordance with an embodiment of the present invention.
Figure 25:
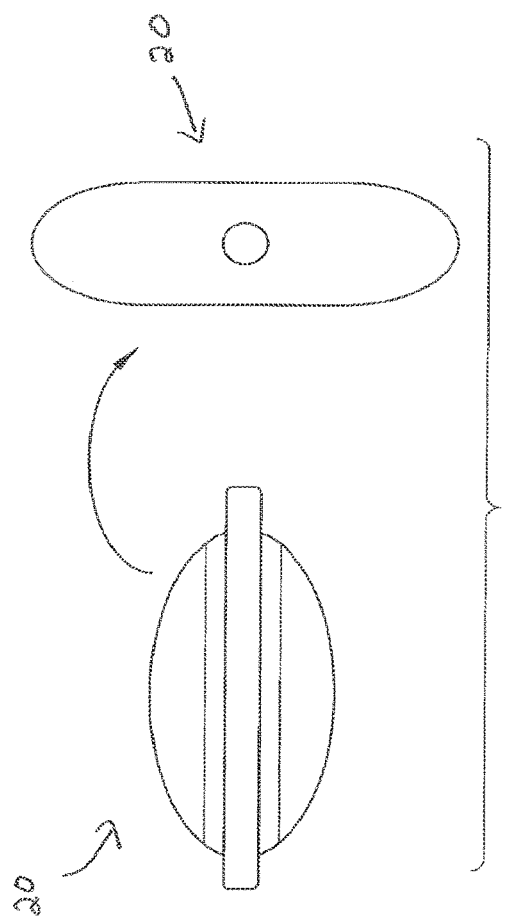
FIG. 25 is a perspective view of a balloon in accordance with an embodiment of the present invention.
Figure 26:
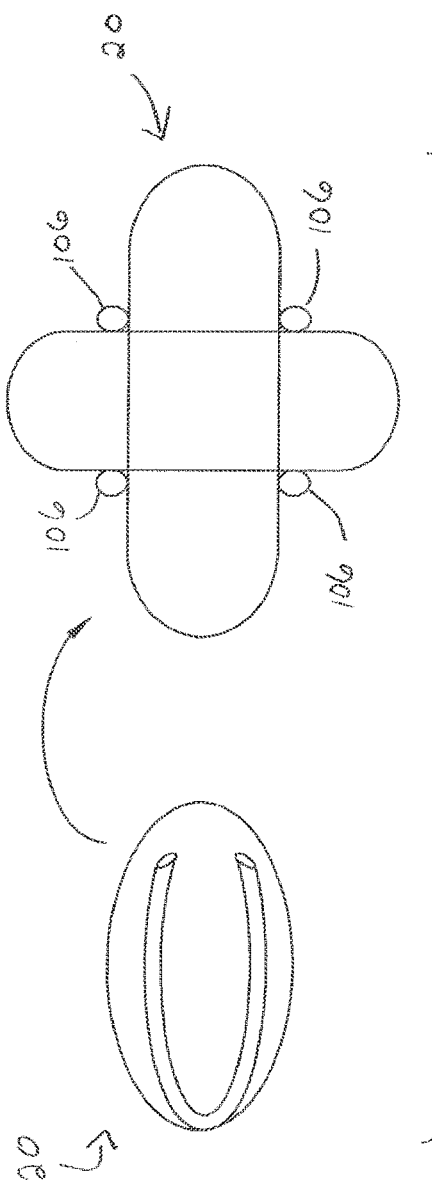
FIG. 26 is a perspective view of a balloon in accordance with another embodiment of the present invention.

Referring to FIGS. 15, 25, and 26, in one exemplary embodiment, the balloon 20 may be of any suitable shape for providing elevation to fragments of the fracture being corrected. However, by providing a balloon 20 having directionality, the elevation of the fragments of the fracture can be provided in a directional manner and the directionality of the space created in the fracture can be tailored for the specific fracture. For example, the balloon 20 may have a longer dimension in a first direction than in another direction, for example an oblong balloon 20 having an oval or rectangular cross-section. The three-dimensional space occupied by the inflated balloon 20 provides support along an axis of compression, giving the operator greater control in the direction of reduction.

Referring to FIGS. 15, 25, and 26, alternatively, in another exemplary embodiment, a biaxial or bipolar balloon having different sizes and/or shapes in different portions of the balloon may be provided. Such a balloon is useful for correction of a fracture requiring the elevation of multiple planes of compression that would benefit from partial or whole inflation in different directions. Such a balloon provides a more complete, precise correction.

Referring to FIGS. 15, 25, and 26, in another exemplary embodiment, a balloon 20 of the present disclosure may be an oblong or oval balloon having a longer diameter in one axis. The balloon 20 may be mounted on the device 10 such that the longer diameter axis is coaxial/parallel to the device handle 30. In this manner, an operator is able to manually position the device 10 to ensure that the longer diameter axis is in the position where the fracture reduction is desired. Deployment of the balloon 20 will result in an oval reduction space along the axis of the fracture, optimizing fracture reduction, while minimizing unwanted fragment expansion along other directions.

Referring to FIG. 26, in an exemplary embodiment, four cement channels 106 with four respective cement outlets are included. In other exemplary embodiments, other configurations of cement channels are envisioned to allow for flexibility in controlling the delivery of cement C to a fracture site 200.

The tip 18 has a sharpened point to allow the device 10 to cut through bone and tissue.

The device 10 may also be provided with a mechanism for controlling the flow of the fluid and the cement C into the cannula 16. The mechanism may be located within the housing 12 with a thumb wheel or other suitable actuator extending through the housing 12, may be located exterior to the housing 12, or may be provided to work in combination with the previously described thumb wheel 84, connection box 28, outer fluid tube 56, and/or inner cement tube 54. The mechanism may be, for example, a three-way valve (not shown) where in a first position, fluid is permitted to flow into or out of the outer fluid tube 56 to inflate or deflate the balloon 20; a second position in which cement C is permitted to flow into the inner cement tube 54; and a third closed position in which neither fluid nor cement C is permitted to flow into the cannula 16. In the third position, the fluid pressure is maintained in the balloon 20 to maintain the balloon 20 at a constant.

Referring to FIGS. 15-24, in order to simultaneously control the fluid provided to the expander/balloon, and the cement C provided to a fracture site 200, a double-barrel fluid and cement controller 120 may be used. A controller 120 of the present disclosure includes a first barrel 132, a second barrel 134, a pressure gauge 122, and a knob 124, that controls a position and configuration of a middle control gear 126, that allows a user to manually control the proportion of fluid and cement C entering the respective passageways 58, 60 of the cannula 16. Referring to FIGS. 15-21, the first fluid inlet 22 is connected to the first barrel 132 via a first line 142 and the second cement inlet 24 is connected to the second barrel 134 via a second line 144. In one embodiment, the first barrel 132 includes a fluid such as saline S and the second barrel 134 includes a cement C. When the knob 124 is in its lowest position (FIG. 23), the controller 120 only releases fluid, for example, to the outer fluid tube 56. Similarly, with the knob 124 at its highest position (FIG. 24), the controller 120 only releases cement C, for example, to the inner cement tube 54. This may be accomplished via a gear system 126, 128, 130 where a middle control gear 126 is controlled by the movement of the knob 124 on the outside of the controller 120. With the knob in its lowest position (FIG. 23), the middle gear 126 only engages a fluid gear 128 controlling the dispensing of the fluid, and, with the knob 124 in the highest position (FIG. 24), the middle gear 126 only engages a cement gear 130 controlling the dispensing of the cement C. At any position of the knob between the lowest position (FIG. 23) and the highest position (FIG. 24), the middle gear 126 proportionally engages both the cement gear 130 and the fluid gear 128, creating different ratios of cement C and fluid that are dispensed. The proportion of fluid to cement C may therefore be adjusted based on the progress of the procedure by adjusting the knob position. A controller 120 of the present disclosure reduces procedure time and semi-automates the task of controlling substance flow during the procedure.

In one embodiment, the controller 120 of the present disclosure is mechanically controlled. In other embodiments, the controller 120 of the present disclosure is motorized controlled, with digital control of the functions of the cement and fluid.

Figure 12:
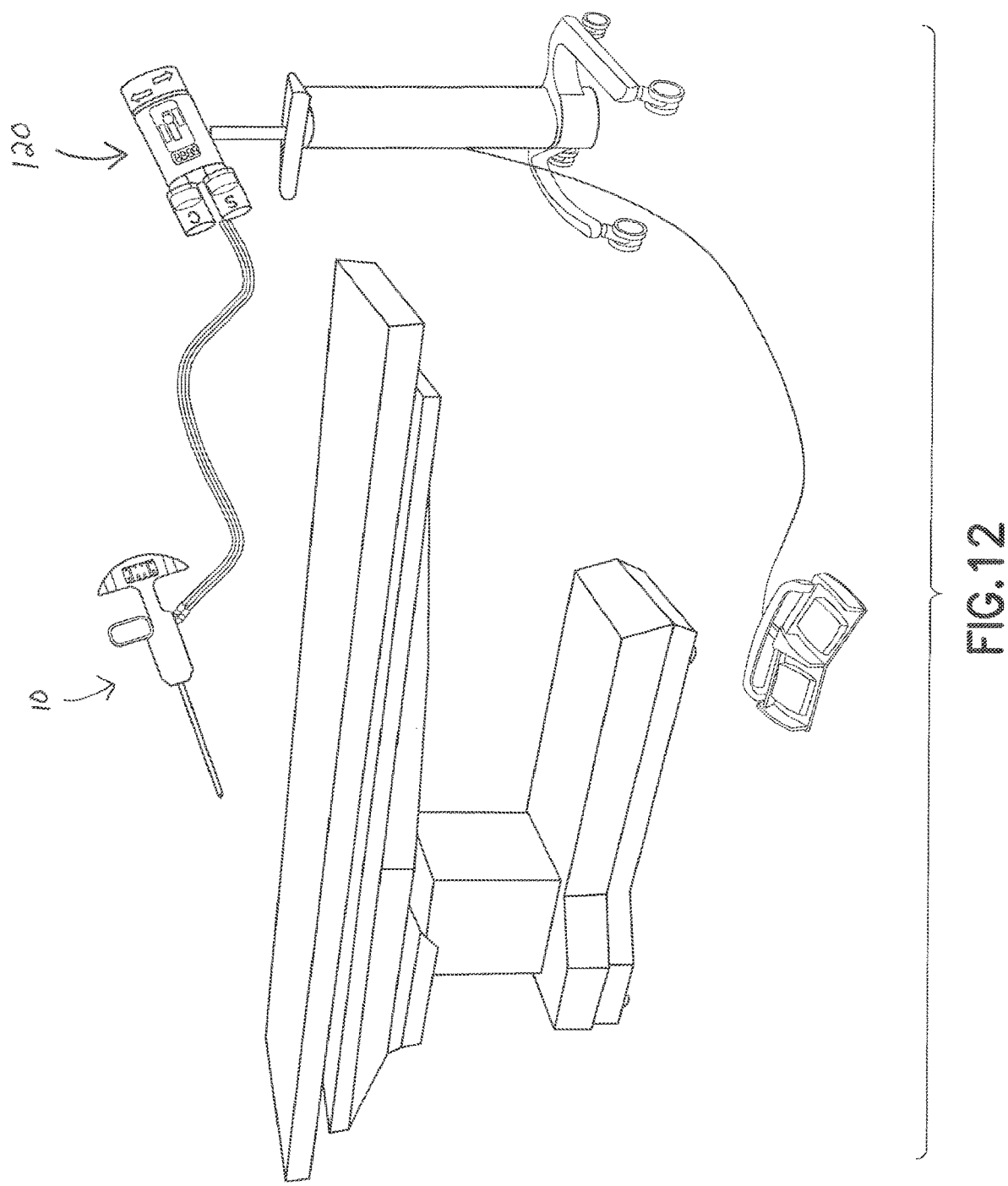
FIG. 12 is a perspective view of a device and system in accordance with an embodiment of the present invention.

Referring to FIGS. 12-21, use of a device 10 of the present disclosure will now be described. Referring to FIG. 12, in an exemplary embodiment, a system including a device 10 of the present disclosure in an operating room setting is shown.

Figure 13:
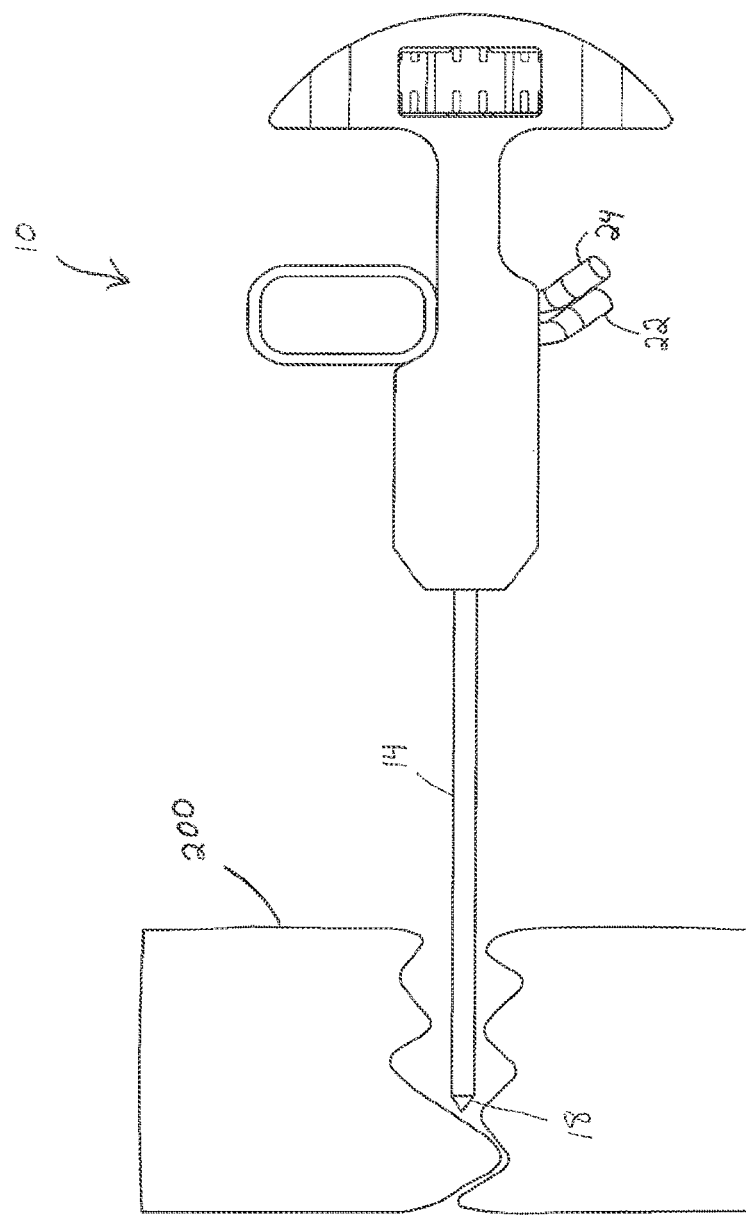
FIG. 13 is a perspective view of a first step of using a device of the present disclosure in accordance with an embodiment of the present invention.
Figure 14:
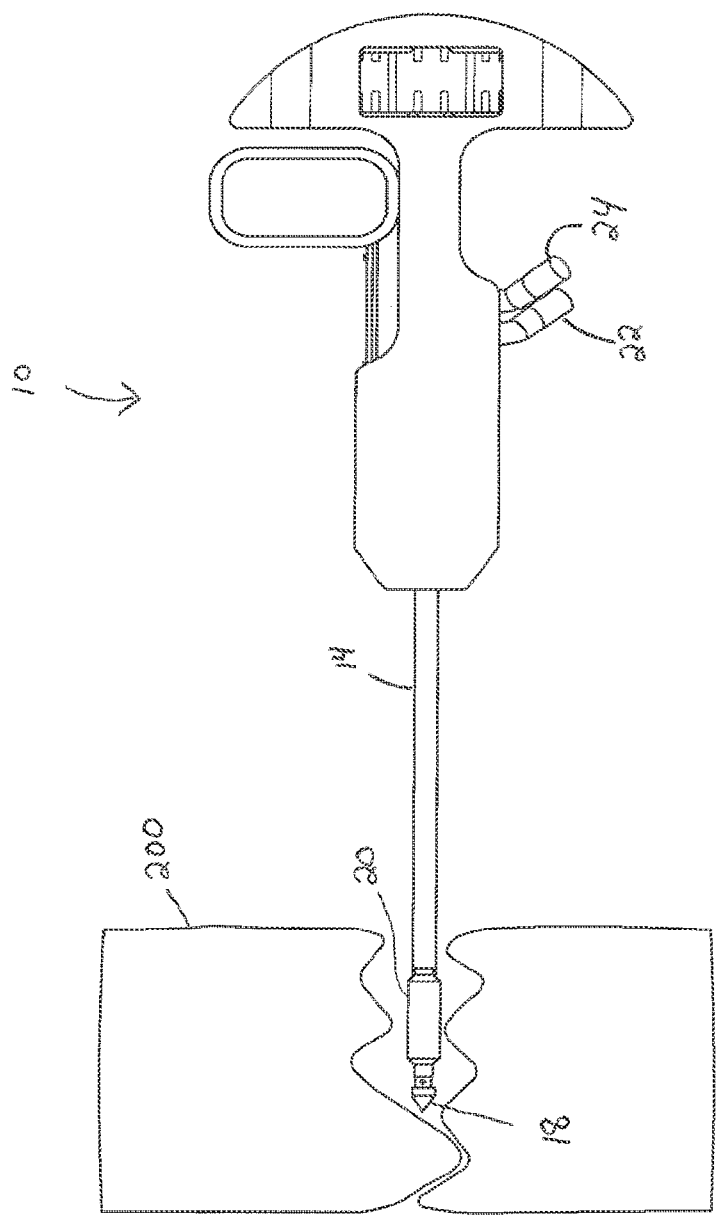
FIG. 14 is a perspective view of a second step of using a device of the present disclosure in accordance with an embodiment of the present invention.

Referring to FIG. 13, in operation, the tip 18 of the device 10 is inserted into a fracture or fracture site 200. Advantageously, the device 10 of the present disclosure allows an operator to control and position the device 10 with only one hand. Referring to FIG. 14, next, one or more of the user's fingers near the top of the device 10 are used to retract the handle 30 to expose the balloon 20 and the distal portion 44 of the cannula 16. The handle 30 is retracted thereby exposing the balloon 20 and the distal portion 44 of the cannula 16.

Referring to FIG. 15, the balloon 20 may then be inflated by starting flow of the fluid through the outer fluid tube 56 and into the balloon 20 to elevate the fragments of the fracture 200 creating a void into which bone cement C may be injected. The three-dimensional space occupied by the inflated balloon 20 provides support along an axis of compression, giving the operator greater control in the direction of reduction.

Figure 16:
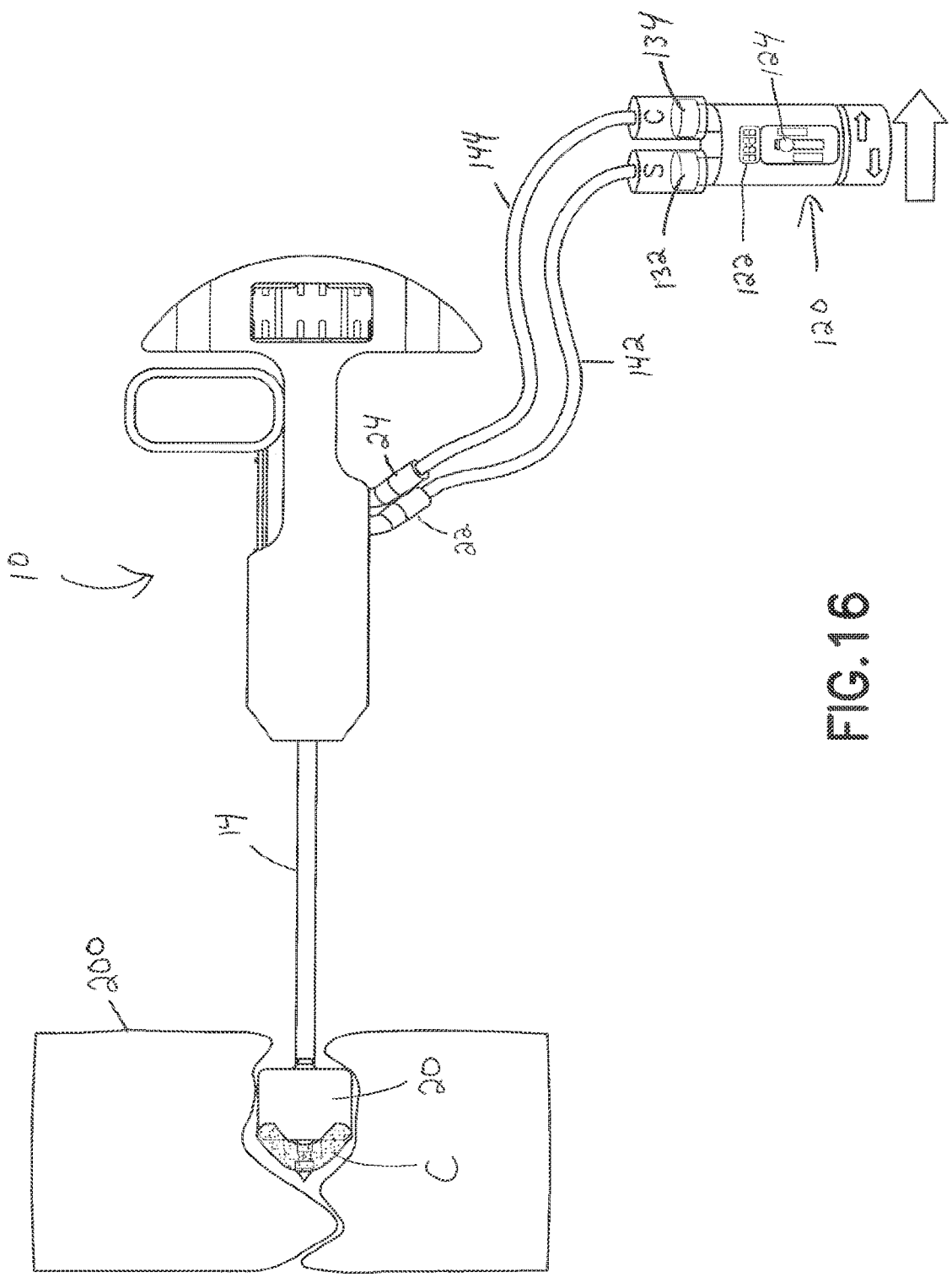
FIG. 16 is a perspective view of a fourth step of using a device of the present disclosure in accordance with an embodiment of the present invention.
Figure 17:
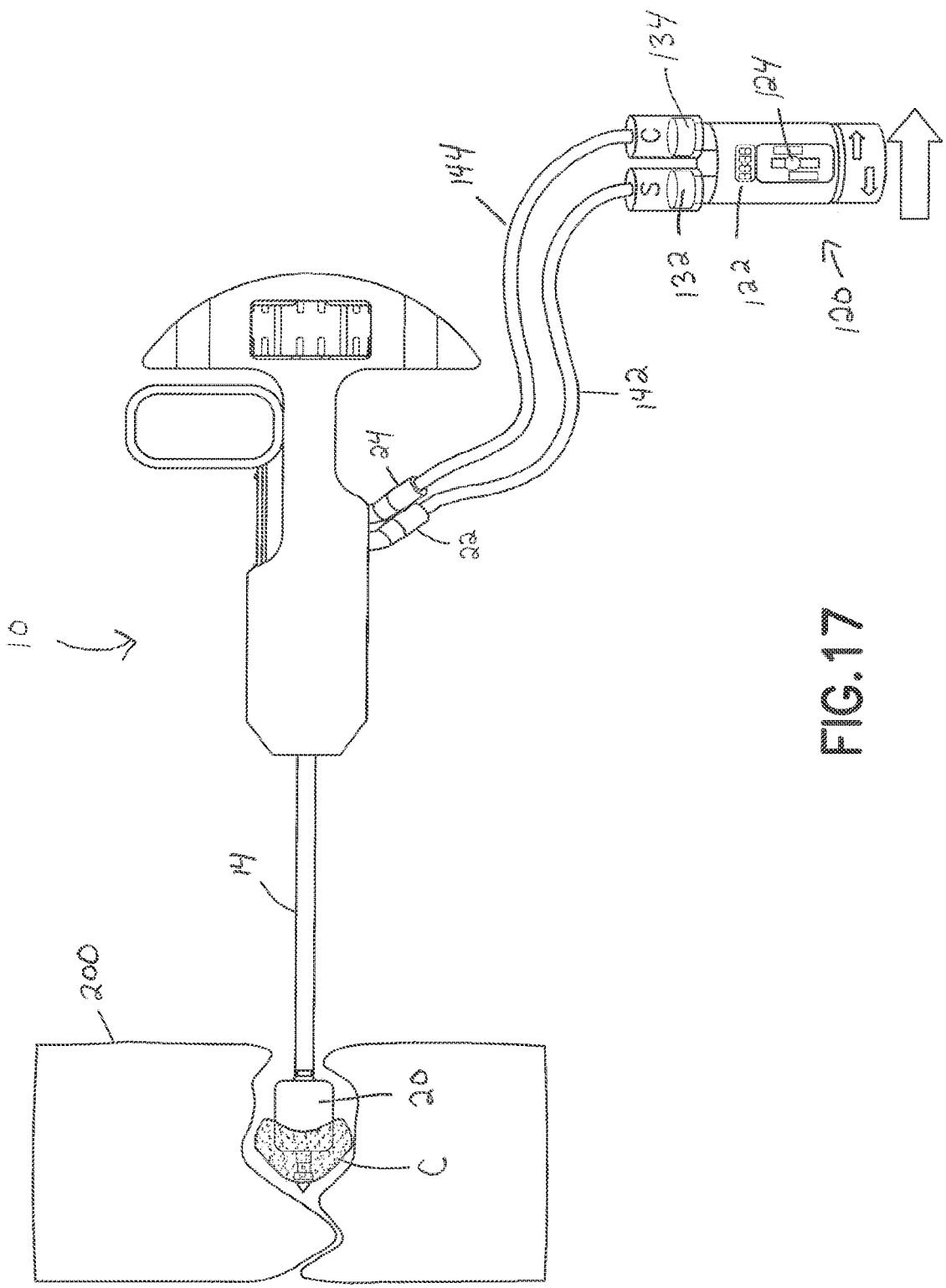
FIG. 17 is a perspective view of a fifth step of using a device of the present disclosure in accordance with an embodiment of the present invention.
Figure 18:
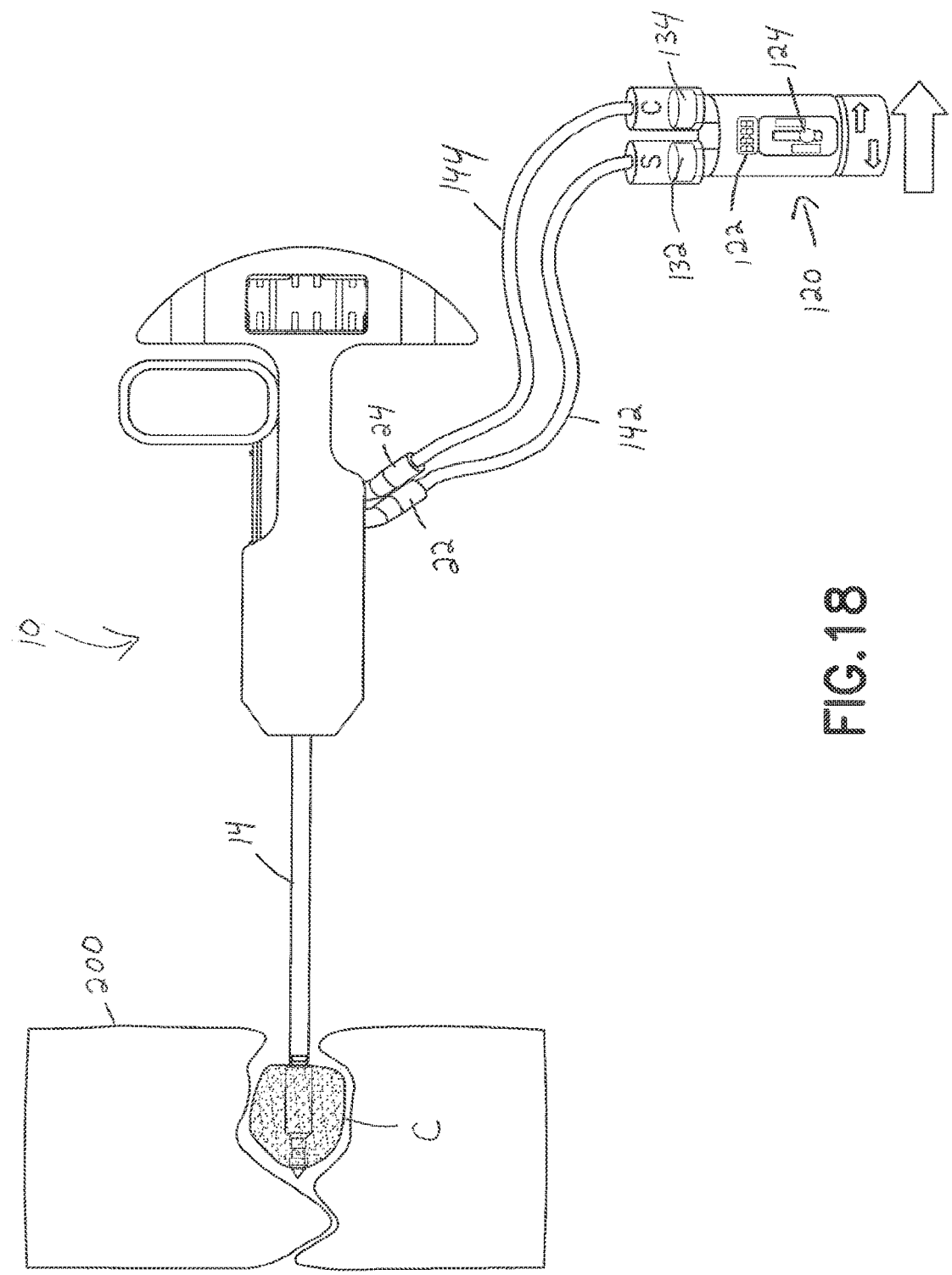
FIG. 18 is a perspective view of a sixth step of using a device of the present disclosure in accordance with an embodiment of the present invention.

Referring to FIGS. 16-18, when the desired elevation has been achieved, the flow of fluid to the balloon 20 may be stopped thereby maintaining a constant pressure in the balloon 20 and a constant elevation in the fragments of the fracture 200. Flow of cement C to the inner cement tube 54 may then be started, and the thumb wheel 84 may be set to provide either axial or radial flow of cement C into the fracture 200. The procedure then continues with cement C being provide either radially or axially after and/or during deflation of the balloon 20. Advantageously, all of the openings for cement injection 74, 76, 78, 96, 100 are provided in the portion of device 10 that is located between the balloon 20 and the distal end 26 of the device 10. In this manner, cement C may be injected into the opening in the fracture 200 created by the balloon 20 while the balloon 20 is still at least partially inflated. This allows the elevation of the fragments within the fracture 200 to be maintained more precisely as the cement C is injected and the device 10 is advanced out of the fracture 200, thereby decreasing the likelihood of procedure failure and reducing procedure time.

Figure 19:
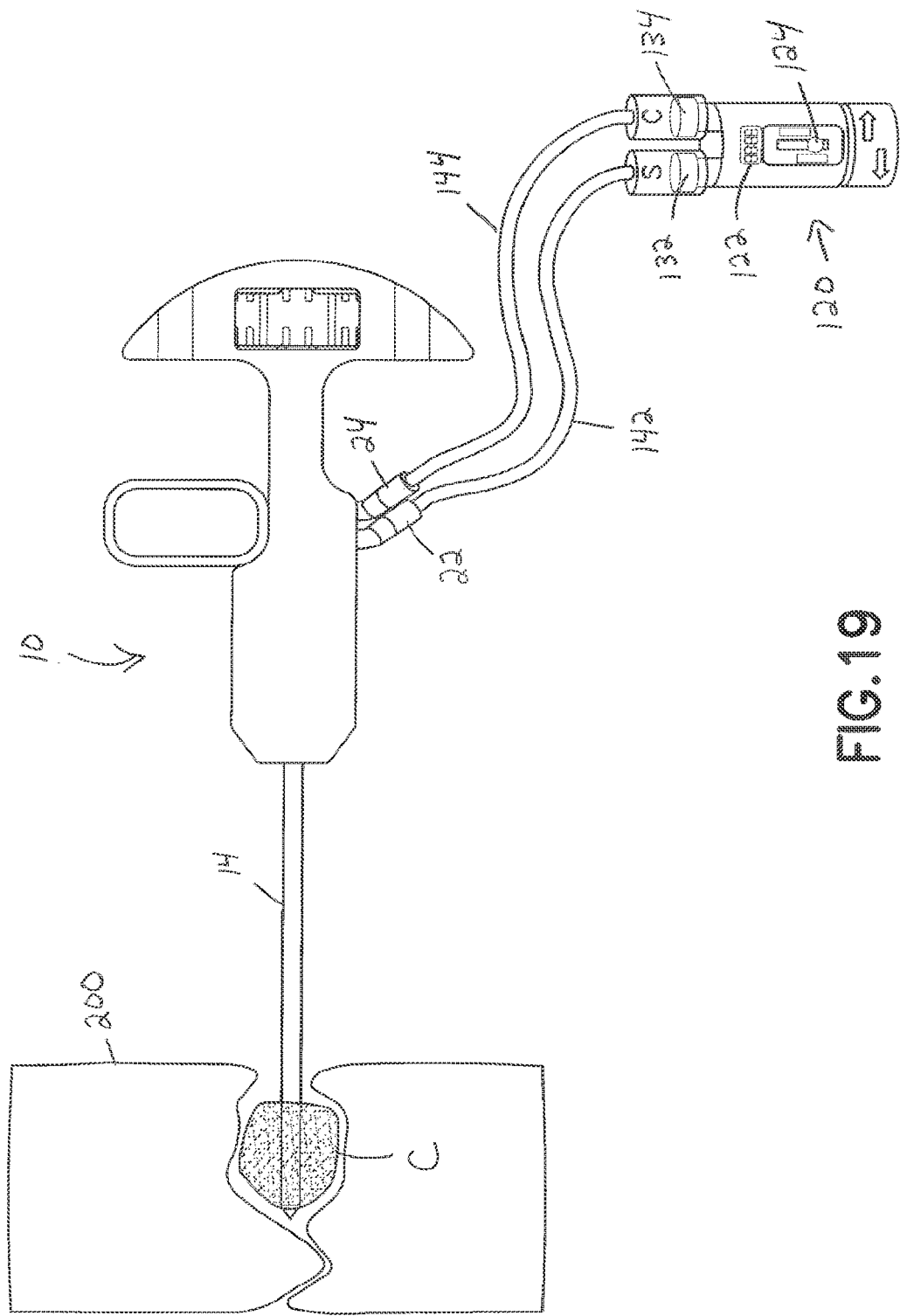
FIG. 19 is a perspective view of a seventh step of using a device of the present disclosure in accordance with an embodiment of the present invention.
Figure 20:
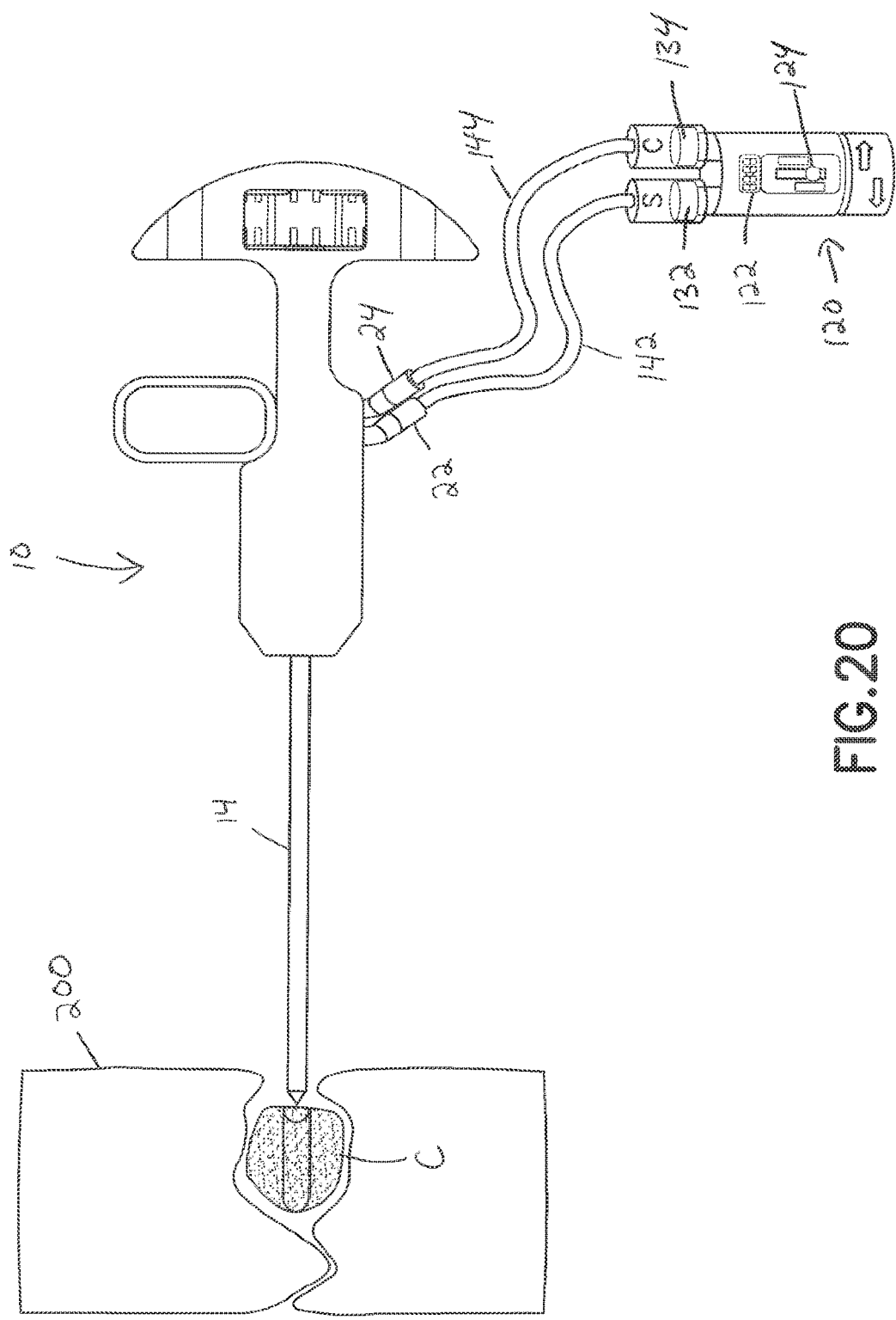
FIG. 20 is a perspective view of an eighth step of using a device of the present disclosure in accordance with an embodiment of the present invention.
Figure 21:
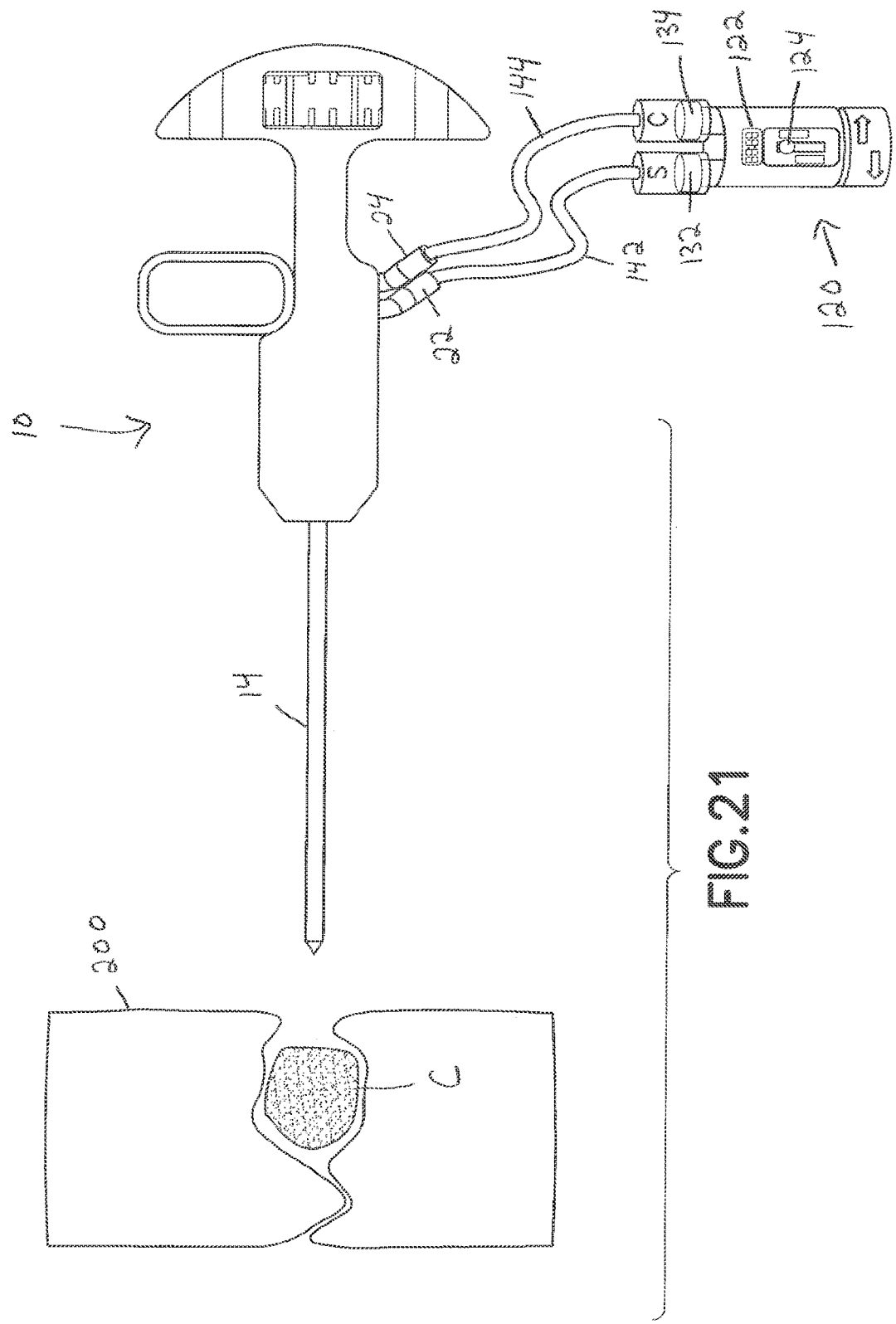
FIG. 21 is a perspective view of a ninth step of using a device of the present disclosure in accordance with an embodiment of the present invention.
Figure 22:
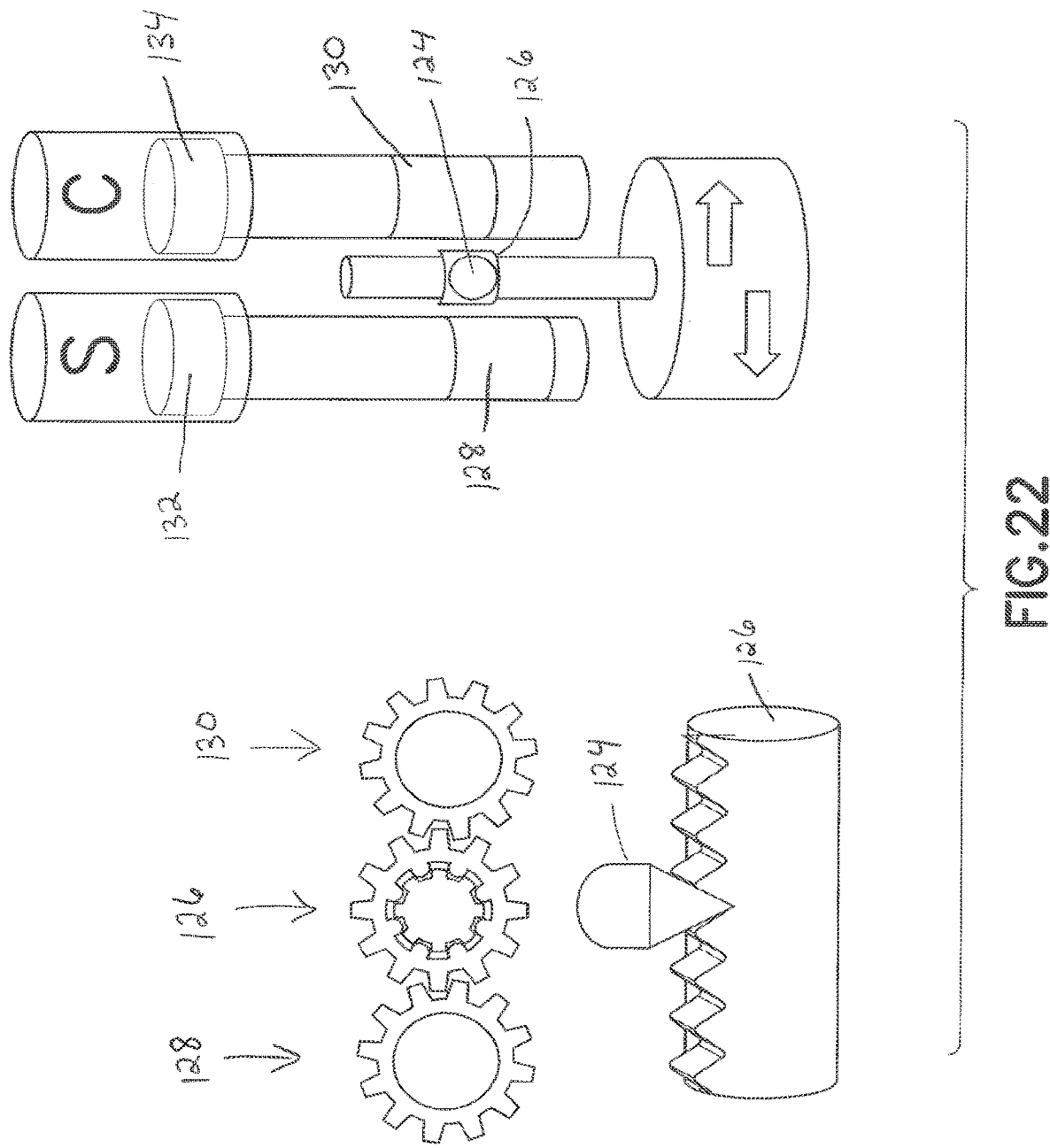
FIG. 22 is a perspective view of a controller in a first position in accordance with an embodiment of the present invention.
Figure 23:
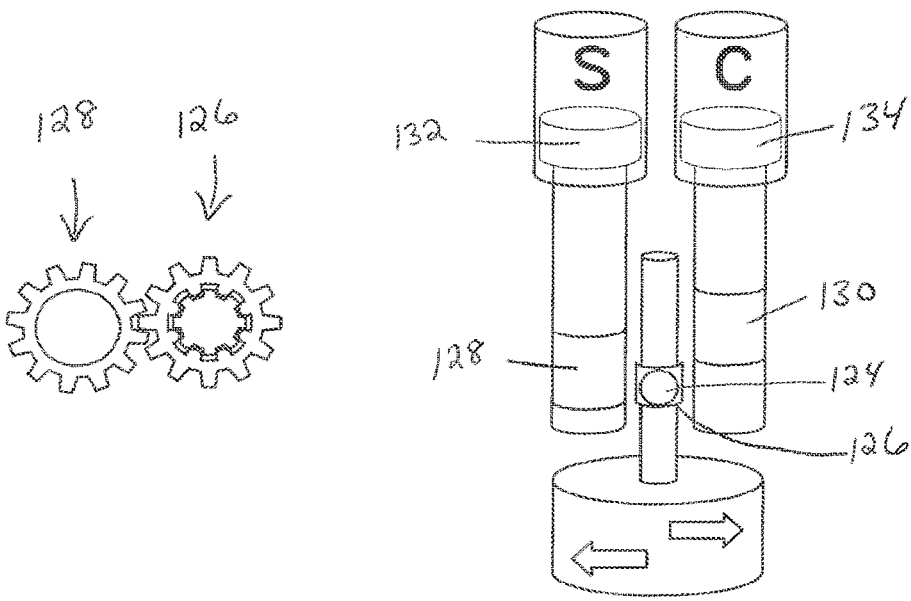
FIG. 23 is a perspective view of a controller in a second position in accordance with an embodiment of the present invention.
Figure 24:
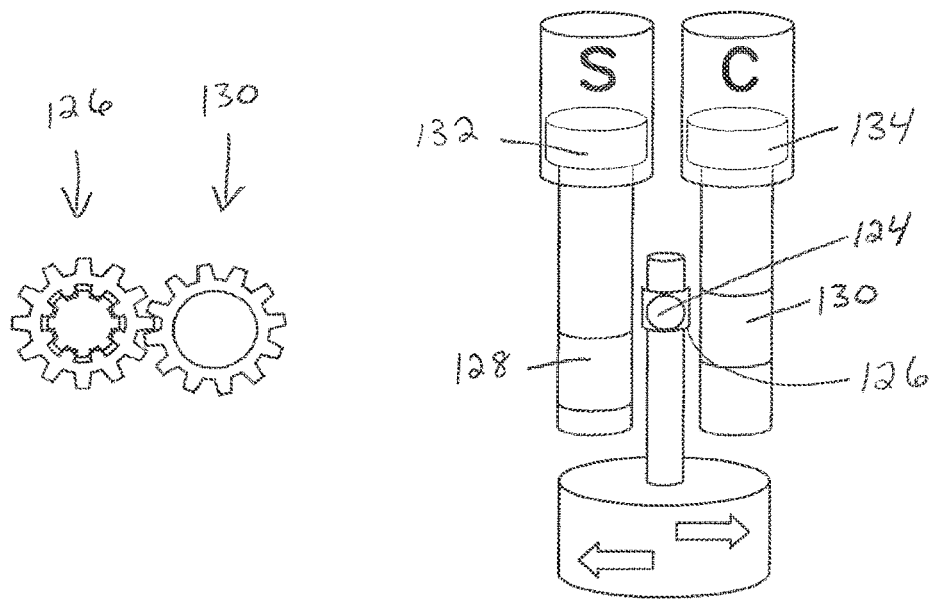
FIG. 24 is a perspective view of a controller in a third position in accordance with an embodiment of the present invention.

Referring to FIGS. 19-21, after the cement C is properly injected into the opening in the fracture 200 created by the balloon 20, the shield 14 is positioned over the balloon 20 and the distal portion 44 of the cannula 16 and the device 10 is removed from the fracture site 200. Additional cement C is delivered to fill the track within the cement C.

Parts of the device may be formed of any of several materials. While the shapes of different components have been depicted as noted, different shapes can be adopted while conforming to the general design principles of the invention.

In certain procedures, and with continued reference to FIGS. 15-21, the operator may achieve fracture reduction in the target area by inflating the balloon 20. The double-barrel fluid and cement controller 120 may display the PSI required to achieve adequate fracture reduction. The operator may then utilize the double-barrel fluid and cement controller 120 to begin cement delivery to the target area. Cement may be delivered to the target area through radial and/or axial openings to provide cement to the precise desired region. Simultaneously, the operator will utilize the double-barrel fluid and cement controller to begin balloon deflation to allow room for cement delivery, while maintaining the desired PSI that was required to achieve fracture elevation, therefore maintaining fracture elevation during cement delivery.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A method of correcting a compression-type fracture comprising:
   inserting a device into a fracture site, the device having a housing having a proximal end and a distal end, a cannula extending from the distal end of the housing and through a directional balloon, and a tip at a distal end of the cannula, wherein the cannula comprises an outer tube for supplying fluid to the balloon and an inner tube positioned within the outer tube for supplying cement through at least one of an axial-opening and a radial opening in the distal end of the cannula, the inner tube includes a cap at a distal end thereof, and the cap has an axial opening and a radial opening;
   inflating the balloon with a fluid supplied through the outer tube to elevate fragments of the fracture;
   injecting cement from the inner tube into the opening created by elevating the fragments of the fracture; and
   removing the device from the fracture site;
   wherein the inner tube is coaxial with the outer tube, a first passageway is defined between the inner tube and the outer tube, a second passageway is defined through the inner tube, and the cap blocks the first passageway.

2. The method of claim 1, wherein the inner tube is rotatable with respect to the outer tube and the tip, the method further comprising rotating the inner tube with respect to the outer tube.

3. The method of claim 2, wherein the tip includes an axial opening and the outer tube of the cannula includes a radial opening.

4. The method of claim 3, wherein depending on the position of the inner tube with respect to the outer tube and the tip, at least one of the radial opening and the axial opening is blocked by the outer tube or the tip.

5. The method of claim 3, wherein the device further comprises a thumb wheel connected to the inner tube and used to rotate the inner tube.

6. The method of claim 5, wherein the thumb wheel can rotate the inner tube into one of three positions:
   a first position where the radial opening of the cap is not aligned with the radial opening of the outer tube and the axial opening of the cap is not aligned with the axial opening of the tip;
   a second position where the radial opening of the cap is aligned with the radial opening of the outer tube and the axial opening of the cap is not aligned with the axial opening of the tip; and a third position where the radial opening of the cap is not aligned with the radial opening of the outer tube and the axial opening of the cap is aligned with the axial opening of the tip.

7. The method of claim 1, wherein the balloon is deflated before the injection of the cement.

8. The method of claim 1, wherein the balloon is deflated simultaneous with the injection of the cement.

9. The method of claim 1, wherein the balloon is elongated such that a length of the balloon in a direction parallel to a longitudinal axis of the cannula is longer than a width of the balloon in a direction transverse to the longitudinal axis of the cannula.

10. The method of claim 2, wherein the outer tube has a hole through which a fluid passes from the first passageway into the balloon.

11. The method of claim 1, wherein the device further comprises a retractable shield that is coaxial with the cannula and covers the cannula and the balloon, and the shield is retracted to expose the balloon and a distal portion of the cannula prior to inflating the balloon.

12. The method of claim 1, wherein the cement is injected in an axial direction.

13. The method of claim 1, wherein the cement is injected in a radial direction.

14. The method of claim 1, further comprising adjusting a flow rate of the fluid supplied to the balloon independently of a flow rate of the cement.

15. The method of claim 1, further comprising adjusting a flow rate of the fluid supplied to the balloon jointly with adjustment of a flow rate of the cement.

16. A method of correcting a compression-type fracture comprising:
   inserting a device into a fracture site, the device having a housing having a proximal end and a distal end, a cannula extending from the distal end of the housing and through a directional balloon, and a tip at a distal end of the cannula, wherein the cannula comprises an outer tube for supplying fluid to the balloon and an inner tube positioned within the outer tube for supplying cement through at least one of an axial-opening and a radial opening in the distal end of the cannula, the inner tube includes a cap at a distal end thereof, and the cap has an axial opening and a radial opening;
   inflating the balloon with a fluid supplied through the outer tube to elevate fragments of the fracture;
   injecting cement from the inner tube into the opening created by elevating the fragments of the fracture; and
   removing the device from the fracture site;
   wherein the balloon is deflated simultaneous with the injection of the cement.

17. A method of correcting a compression-type fracture comprising:
   inserting a device into a fracture site, the device having a housing having a proximal end and a distal end, a cannula extending from the distal end of the housing and through a directional balloon, and a tip at a distal end of the cannula, wherein the cannula comprises an outer tube for supplying fluid to the balloon and an inner tube positioned within the outer tube for supplying cement through at least one of an axial-opening and a radial opening in the distal end of the cannula, the inner tube includes a cap at a distal end thereof, and the cap has an axial opening and a radial opening;
   inflating the balloon with a fluid supplied through the outer tube to elevate fragments of the fracture;
   injecting cement from the inner tube into the opening created by elevating the fragments of the fracture; and
   removing the device from the fracture site;
   wherein the inner tube is rotatable with respect to the outer tube and the tip, the method further comprising rotating the inner tube with respect to the outer tube; and
   wherein the device further comprises a thumb wheel connected to the inner tube and used to rotate the inner tube.

* * * * *

UNITED STATES PATENT AND TRADEMARK OFFICE
CERTIFICATE OF CORRECTION

PATENT NO. : 12,329,431 B2
APPLICATION NO. : 18/492213
DATED : June 17, 2025
INVENTOR(S) : Wael Abo-Auda et al.

It is certified that error appears in the above-identified patent and that said Letters Patent is hereby corrected as shown below:

In the Claims

Column 13, Line 14, Claim 10, delete "claim 2," and insert -- claim 1, --

Signed and Sealed this
Twelfth Day of August, 2025

Coke Morgan Stewart
*Acting Director of the United States Patent and Trademark Office*